(12) United States Patent
Yamaguchi et al.

(10) Patent No.: US 8,995,615 B2
(45) Date of Patent: Mar. 31, 2015

(54) SPECIMEN INFORMATION ACQUISITION SYSTEM

(71) Applicant: Canon Kabushiki Kaisha, Tokyo (JP)

(72) Inventors: Kimiaki Yamaguchi, Tokyo (JP); Toru Den, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 83 days.

(21) Appl. No.: 13/956,623

(22) Filed: Aug. 1, 2013

(65) Prior Publication Data

US 2014/0037054 A1 Feb. 6, 2014

(30) Foreign Application Priority Data

Aug. 2, 2012 (JP) ................. 2012-172012

(51) Int. Cl.
*G01N 23/04* (2006.01)
*G01N 23/02* (2006.01)
*G21K 1/02* (2006.01)
*H05G 1/70* (2006.01)

(52) U.S. Cl.
CPC ................ *G01N 23/02* (2013.01); *G01N 23/04* (2013.01); *G21K 1/02* (2013.01); *H05G 1/70* (2013.01)
USPC ........................................... 378/62; 378/147

(58) Field of Classification Search
CPC ................................ A61B 6/484; G01N 23/04
USPC .................... 378/36, 51, 62, 84, 85, 145, 156
See application file for complete search history.

(56) References Cited

U.S. PATENT DOCUMENTS

2010/0054415 A1 3/2010 Olivo et al.

FOREIGN PATENT DOCUMENTS

JP 2010502977 A 1/2010
JP 2011200532 A 10/2011

*Primary Examiner* — Courtney Thomas
(74) *Attorney, Agent, or Firm* — Canon USA Inc. IP Division

(57) ABSTRACT

A specimen information acquisition system is provided with a first grating which divides divergent X-rays from an X-ray source to form a plurality of primary X-ray beams, and a second grating which blocks at least a part of each of the primary X-ray beams to form a plurality of secondary X-ray beams. The specimen information acquisition system is further provided with an X-ray detector which detects the secondary X-ray beams and a calculator which calculates information of a specimen arranged between the X-ray source and the X-ray detector. The primary X-ray beams do not overlap each other on each of X-ray transmitting portions of the second grating. The edges of the respective primary X-ray beams enter a plurality of X-ray blocking portions of the second grating.

17 Claims, 12 Drawing Sheets

SPECIMEN INFORMATION ACQUISITION SYSTEM

BACKGROUND OF THE INVENTION

1. Field of the Invention

The present invention relates to a specimen information acquisition system.

2. Description of the Related Art

X-ray phase imaging is a method in which the phase change of X-rays caused by a specimen is detected to thereby acquire an image regarding the specimen on the basis of the detection result. There has been proposed an X-ray phase imaging method such as one described in Japanese Patent Application National Publication (Laid-Open) (Translation of PCT Application) No. 2010-502977 (corresponding to US2010/0054415). In this method, the amount of refraction of X-rays caused by a specimen is detected to thereby acquire information regarding the phase change of the X-rays by utilizing the fact that X-rays are refracted by the phase change thereof caused by a specimen.

The principal of this method will be briefly described. In the method, X-rays are, at first, spatially divided by a grating having blocking portions which block X-rays and transmitting portions which transmit X-rays therethrough. The thus divided X-rays become X-ray beams. The X-ray beams are directed to a specimen, and the X-ray beams which have passed through the specimen are detected by an X-ray detector (hereinafter, may just be referred to as a detector). This makes it possible to find out how far the positions of the respective X-ray beams incident on the detector are displaced by the specimen. Further, information regarding the refraction of the X-ray beams caused by the specimen can be obtained on the basis of the displacement amount. A specimen may be arranged between an X-ray source and a grating, and X-rays refracted by the specimen may be divided by the grating.

When performing X-ray phase imaging according to the above method, the phase detection sensitivity of an X-ray beam is generally improved when using an X-ray beam having a smaller width. This is because of that since the amount of refraction of an X-ray beam caused by a specimen does not depend on the width of the X-ray beam, the smaller the width of the X-ray beam is, the larger the displacement amount of the X-ray beam with respect to the width thereof becomes.

In order to make the width of an X-ray beam smaller, the size of an effective focal point (hereinafter, a focal point indicates an effective focal point) of an X-ray source should be reduced. However, in a common X-ray source, the focal point (hereinafter, also referred to as an X-ray focal point) thereof vibrates during the generation of X-rays. The vibration of the X-ray focal point leads to the increase of the apparent area of the X-ray focal point. Since the vibration of the X-ray focal point results from the expansion of an anticathode which is caused by heat generated when electrons are applied to the anticathode and the shrinkage thereof caused by cooling, the irregular deviation of a rotation axis which supports an rotating anticathode, the vibration of the body of the X-ray source, and the like, it is difficult to completely eliminate the vibration of the X-ray focal point. In the present specification, displacement of the X-ray focal point, the displacement having no particular period caused by the aged deterioration of the X-ray source and the like, is also regarded as the vibration. Further, when electrons are applied to the anticathode, the applied electrons are scattered inside the anticathode due to the interaction between atoms constituting the anticathode and the applied electrons. Since the scattered electrons cause unevenness in the luminance of the X-ray focal point, the smaller the size of the effective focal point becomes, the closer the intensity distribution becomes to a normal distribution from a rectangular distribution. In the present specification, a part of the X-ray focal point in which the luminance is low is referred to as a hem. The width of each of the X-ray beams incident on the detector becomes larger due to the influence of the hem. As a result, an overlapping portion is formed between adjacent X-ray beams. The overlapping between the adjacent X-ray beams incident on the detector hinders the detection of the displacement amount of each of the X-ray beams. The hem of the X-ray focal point also has no relation to the size of the effective focal point as with the vibration amount. Therefore, the smaller the size of the effective focal point becomes, the relatively larger the influence of the hem of the X-ray focal point on the width of each of the X-ray beams becomes.

Japanese Patent Application Laid-open No. 2011-200532 discloses an X-ray imaging system in which the application period of electrons applied to an anticathode is synchronized with the rotation period of the anticathode for reducing the increase of the apparent area of an X-ray focal point caused by the vibration of the X-ray focal point. Further, Japanese Patent Application Laid-open No. 2011-200532 discloses an X-ray imaging system including a shutter which is provided outside an X-ray source, and opens and closes at the same period as the rotation period of an anticathode.

However, although the X-ray imaging system disclosed in Japanese Patent Application Laid-open No. 2011-200532 solve the problem of vibration of the focal point, the vibration having the same period as the rotation period of the anticathode of the X-ray source, the influence by the scattering of the electrons applied to the anticathode is not taken into consideration.

SUMMARY OF THE INVENTION

Therefore, the present invention provides a specimen information acquisition system that acquires information of a specimen using an X-ray beam and is capable of reducing the increase of the width of the X-ray beam caused by the scattering of electrons applied to an anticathode of an X-ray source.

An embodiment of the present invention provides a specimen information acquisition system comprising a first grating having X-ray transmitting portions and X-ray blocking portions, the first grating dividing divergent X-rays from an X-ray source to form a plurality of primary X-ray beams; a second grating having X-ray transmitting portions and X-ray blocking portions, the second grating blocking at least a part of each of the plurality of primary X-ray beams to form a plurality of secondary X-ray beams; and an X-ray detector detecting the plurality of secondary X-ray beams, wherein the plurality of primary X-ray beams do not overlap each other on each of the X-ray transmitting portions of the second grating, and the first grating and the second grating are arranged so that edges of the plurality of primary X-ray beams enter the X-ray blocking portions of the second grating.

Further features of the present invention will become apparent from the following description of exemplary embodiments (with reference to the attached drawings).

DESCRIPTION OF THE EMBODIMENTS

Figure 12:
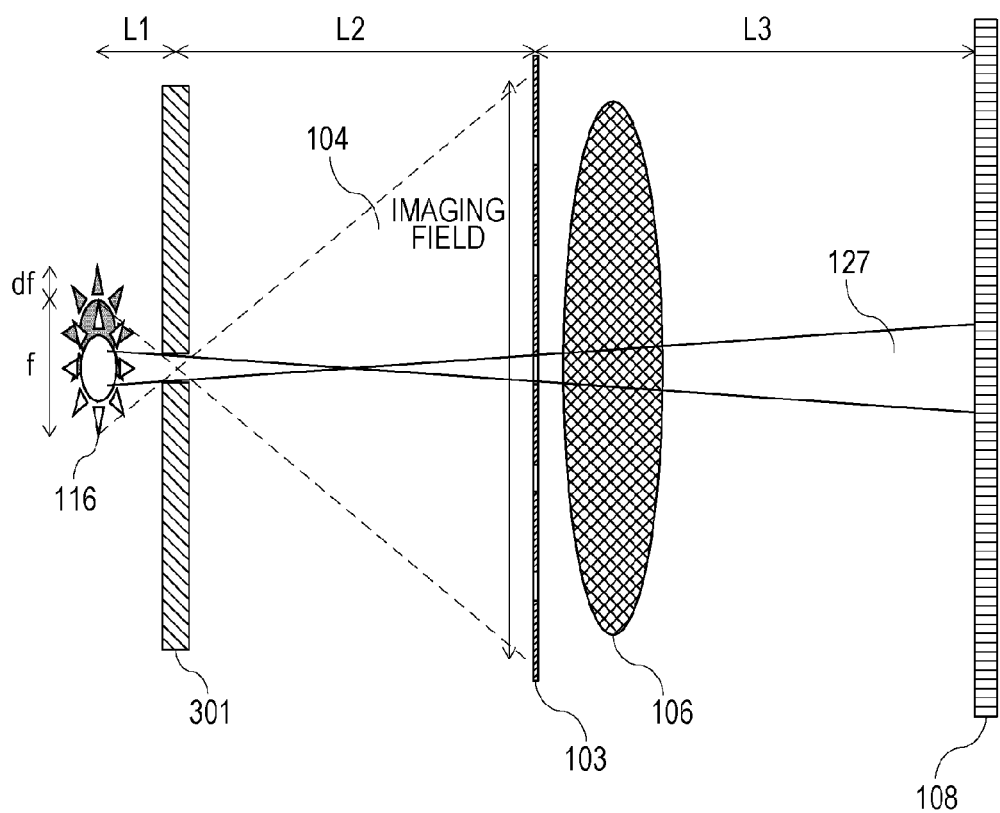
FIG. 12 is a schematic view of a specimen information acquisition system including a collimator installed therein.

The inventors of the present application have developed a specimen information acquisition system as shown in FIG. 12 in order to reduce the increase of the width of an X-ray beam caused by the increase of the apparent area of an X-ray focal point due to vibration of the X-ray focal point and the enlargement of an X-ray generating region due to the scattering of electrons applied to a target of X-ray source. The specimen information acquisition system of FIG. 12 includes a collimator 301 which is installed between an X-ray focal point 116 and a grating 103. In the present specification, the collimator 301 has a single hole. By using the collimator 301, a region of the X-ray focal point 116 from which X-rays contributing to an X-ray beam 127 which enters an X-ray detector 108 are emitted can be made narrow. As a result, it is possible to reduce the increase of the width of the X-ray beam caused by the vibration of the X-ray focal point and the scattering of the applied electrons.

This is because of that, when considering the intensity distribution of X-rays emitted from the focal point and the intensity distribution of X-rays emitted from a region in which the X-rays are generated due to the scattering of the applied electrons, the intensity distribution of X-rays emitted from the region in which the X-rays are generated due to the scattering of the applied electrons often has a shape like a hem of the intensity distribution of X-rays emitted from the focal point. In the present specification, a range in which the intensity is 50% or more of a maximum value of the intensity distribution of the X-ray focal point 116 is defined as a focal point. Further, a range in which the intensity is less than 50%, but larger than 0% of the maximum value is referred to as a hem. In a conventional specimen information acquisition system, uneven X-ray irradiation may occur due to the influence of the hem.

Further, the use of this technique makes it possible to use not only an X-ray source having a rotating anticathode such as one described in Japanese Patent Application Laid-open No. 2011-200532, but also an X-ray source having a fixed-type anticathode or a transmission-type anticathode.

However, in order to ensure the area of an imaging field (an imaging range) with the collimator 301 having only the single opening, it is necessary to design the system so that the distance between the X-ray focal point 116 and the collimator 301 is approximately a few millimeters. For example, assuming that the effective focal point size of the X-ray focal point 116 is 300 μm, the distance between the X-ray focal point 116 and the grating 103 is 100 cm and the imaging field is 30 cm, the distance between the X-ray focal point 116 and the collimator 301 becomes approximately 1 mm.

However, when the collimator 301 is placed at a position 1 mm away from the X-ray focal point 116 in an X-ray source 101 having a fixed-type anticathode or a rotating anticathode, the collimator 301 may disturb the focusing of electrons applied from the X-ray source 101 or may cause the discharge of the electrons. In order to prevent such problems, it is necessary to set the distance between the X-ray focal point 116 and the collimator 301, for example, at approximately 5 cm, although it depends on the size of an X-ray tube. In this case, the imaging field disadvantageously becomes small up to approximately 5 mm.

In view of the above, the inventors of the present application have invented a specimen information acquisition system that is provided with not a collimator having a single opening, but a diving element which has a plurality of openings and is arranged between an X-ray focal point and another grating. Accordingly, it is possible to expand the imaging field compared to the system using the collimator, while reducing the increase of the width of an X-ray beam caused by the vibration of the X-ray focal point and the scattering of the applied electrons.

Hereinafter, preferred embodiments of the present invention will be described with reference to the attached drawings. Throughout the drawings, the same reference numerals are used to refer to the same components, and a description thereof will be omitted.

In the present invention and the present specification, Fresnel diffraction which occurs when X-rays pass through a grating is not taken into consideration for the purpose of simplifying calculations and models of the embodiments. Further, when a plurality of gratings, for example, four gratings, are used in a single specimen information acquisition system, the four gratings are referred to as a first grating, a second grating, a third grating and a fourth grating in this order from the one closest to the X-ray source and the X-ray focal point.

(First Embodiment)

Figure 1:
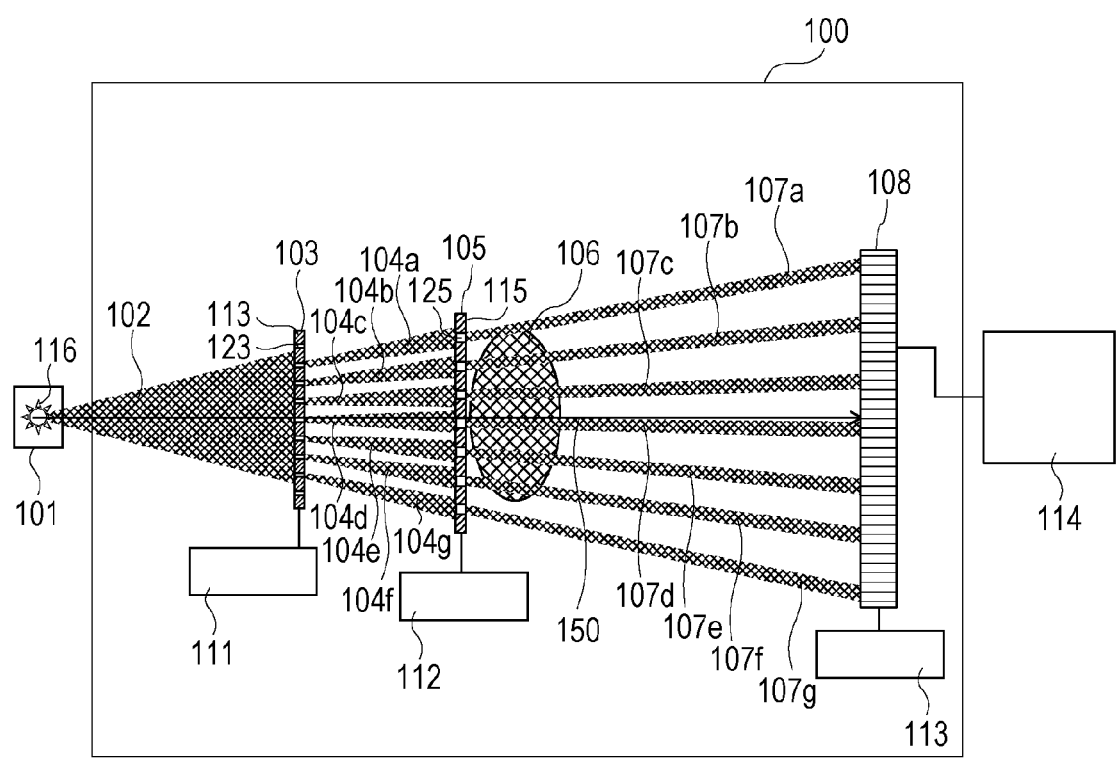
FIG. 1 is a schematic view of a specimen information acquisition apparatus according to a first embodiment of the present invention.

FIG. 1 illustrates a schematic view of a specimen information acquisition system according to a first embodiment. The specimen information acquisition system is not limited to one acquiring an image of a specimen as long as it is capable of acquiring information of the specimen.

A specimen information acquisition system 100 shown in FIG. 1 is provided with a first grating 103 and a second grating 105. The first grating 103 divides divergent X-rays 102 from an X-ray source 101 to thereby form a plurality of primary X-ray beams 104 (primary X-ray beams 104a to 104g). Herein, a divergent X-ray indicates a general divergent X-ray such as a cone beam and a fan beam. The second grating 105 forms secondary X-ray beams 107 (secondary X-ray beams 107a to 107g) from the primary X-ray beams 104. In addition, the specimen information acquisition system 100 is further provided with a detector 108 which detects the secondary X-ray beams 107 formed by the second grating 105. Since the specimen information acquisition system 100 of FIG. 1 is provided with only two gratings, the secondary X-ray beams 107 enter the detector 108. However, when the specimen information acquisition system is provided with three or more gratings, X-ray beams that are formed by one of the gratings, the one being closest to the detector, enter the detector. In the present invention and the present specification, even when the secondary X-ray beams do not enter the detector as just described, it is regarded that the detector indirectly detects the secondary X-ray beams. Therefore, in the present invention and the present specification, detecting the secondary X-ray beams also includes detecting tertiary or higher-order X-ray beams which are formed using the secondary X-ray beams. Further, the specimen information acquisition system 100 is also provided with a first moving unit 111 as moving means for the first grating 103 and a second moving unit 112 as moving means for the second grating 105. A specimen 106 is arranged between the second grating 105 and the detector 108 in FIG. 1. However, the specimen 106 may be arranged at any positions between the X-ray source 101 and the detector 108. For example, the specimen 106 may be arranged between the first grating 103 and the second grating 105, or between the X-ray source 101 and the first grating 103.

Further, an X-ray imaging system according to the present embodiment is constructed from the specimen information acquisition system 100, the X-ray source 101 and a calculator 114 as calculation means which calculates information of a specimen on the basis of a detection result obtained by the detector.

The X-ray source 101 may have any configuration as long as it has an X-ray focal point 116 and can direct the divergent X-rays to the first grating. As described above, any of a rotating anticathode, a fixed-type anticathode and a transmission-type anticathode can be used as the anticathode of the X-ray source 101. Further, in the present specification, one of axes that connect the X-ray focal point 116 of the X-ray source 101 with the detector 108, the one having the shortest distance, is referred to as an optical axis 150.

The first grating 103 has X-ray transmitting portions (hereinafter, may just be referred to as transmitting portions) and X-ray blocking portions (hereinafter, may just be referred to as blocking portions), and spatially divides the divergent X-rays 102 from the X-ray source 101 to thereby form the plurality of primary X-ray beams 104. The first grating 103 used in the present embodiment has the same structure as the structure of a focusing grid which is used for eliminating scattered X-rays which are generated when imaging a specimen in a medical X-ray imaging system. In this structure, X-ray transmitting portions which are made of a light element having a high X-ray transmittance and X-ray blocking portions which are made of a heavy element having a low X-ray transmittance are alternately arranged. For example, aluminum, paper, synthetic resins and the like are used as the constituent material of the X-ray transmitting portions, and platinum, gold, lead, tantalum, tungsten and the like are used as the constituent material of the X-ray blocking portions. Further, the X-ray transmitting portions may be voids as long as they can maintain gaps between the X-ray blocking portions. The second grating 105 has the same structure as the structure of the first grating 103, and can be composed of the same materials as the constituent materials of the first grating 103. Each of the constituent material of the X-ray transmitting portions and the constituent material of the X-ray blocking portions does not have to be the same between the first grating 103 and the second grating 105.

In each of the gratings, the width of each of the X-ray transmitting portions is denoted by Ga, and the width of each of the X-ray blocking portions is denoted by Gb. Further, the thickness of each of the gratings is denoted by t. In particular, the width of each of the X-ray transmitting portions of the first grating 103 is denoted by Ga1, the width of each of the X-ray blocking portions thereof is denoted by Gb1, and the thickness thereof is denoted by t1. Further, the width of each of the X-ray transmitting portions of the second grating 105 is denoted by Ga2, the width of each of the X-ray blocking portions thereof is denoted by Gb2, and the thickness thereof is denoted by t2. Each of the width of an X-ray transmitting portion and the width of an X-ray blocking portion is the length thereof with respect to the alignment direction of the X-ray transmitting portions and the X-ray blocking portions in a plane that is in contact with a surface of a grating, the surface facing the X-ray source, and is perpendicular to the optical axis. Further, in the present specification, a surface of each of the gratings, the surface facing the X-ray source (a surface located at the upstream side of an optical path), is referred to as a front surface, and the other surface facing the detector (a surface located at the downstream side of the optical path) is referred to as a back surface.

In the first grating 103 used in the present embodiment, it is preferred that Ga1 be within the range of 1 μm to 200 μm, Gb1 be within the range of 2 μm to 390 μm, Ga1+Gb1 be within the range of 5 μm to 400 μm, and t1 be within the range of 10 μm to 2 mm. Similarly, in the second grating 105, it is preferred that Ga2 be within the range of 1 μm to 200 μm, Gb2 be within the range of 2 μm to 990 μm, Ga2+Gb2 be within the range of 5 μm to 1000 μm, and t2 be within the range of 10 μm to 2 mm.

Figure 2:
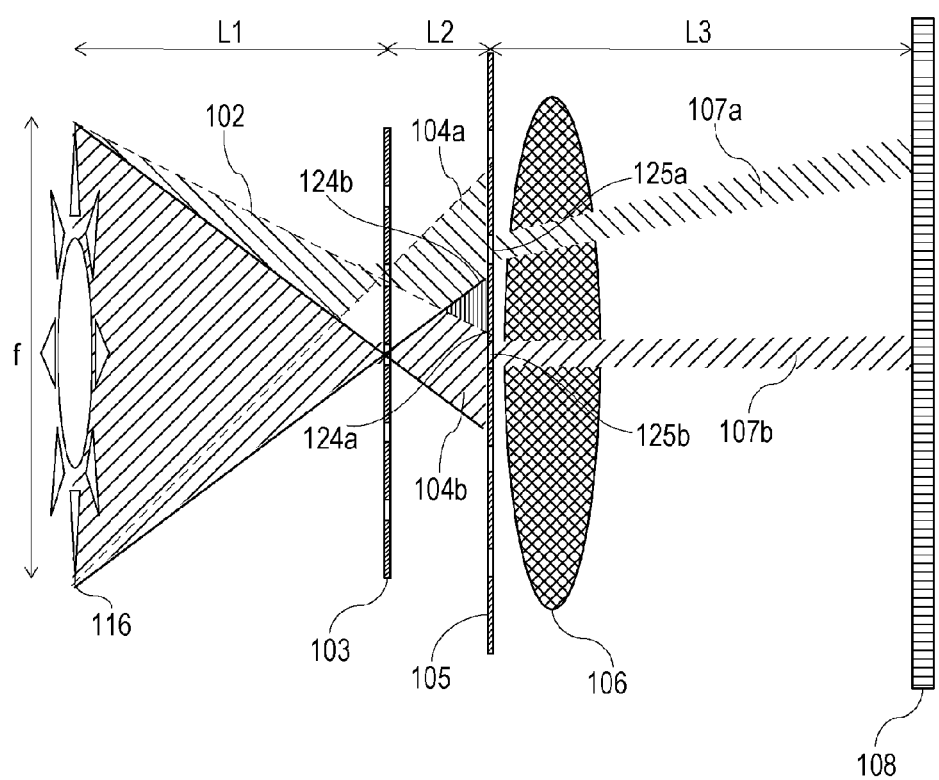
FIG. 2 is a schematic view of the positional relationship between an X-ray focal point and gratings according to the first embodiment of the present invention.
Figure 3A:
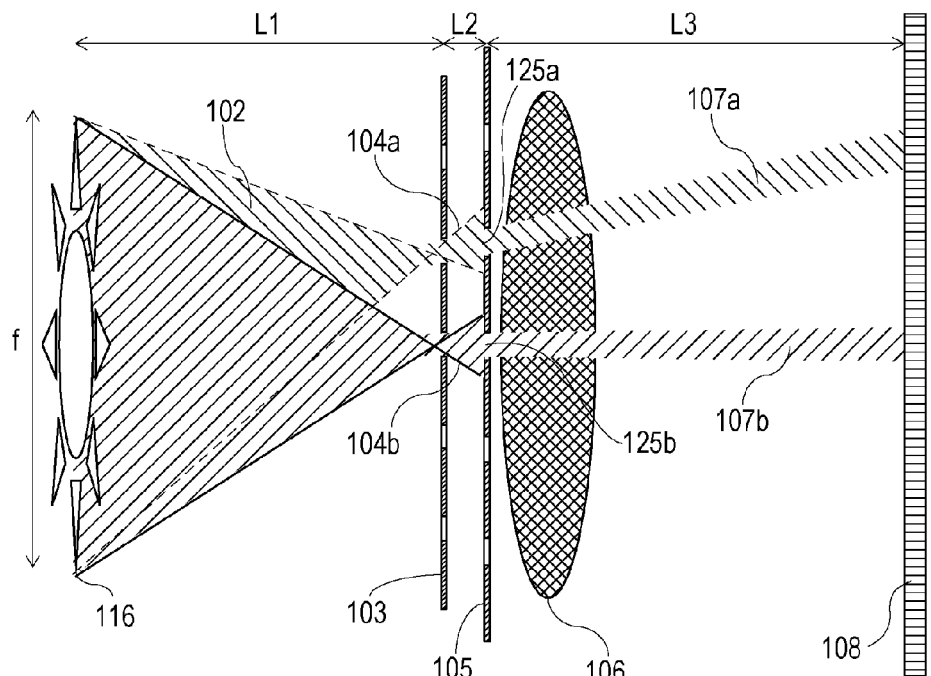
FIGS. 3A and 3B are schematic views of the positional relationship between the X-ray focal point and the gratings according to the first embodiment of the present invention.
Figure 3B:
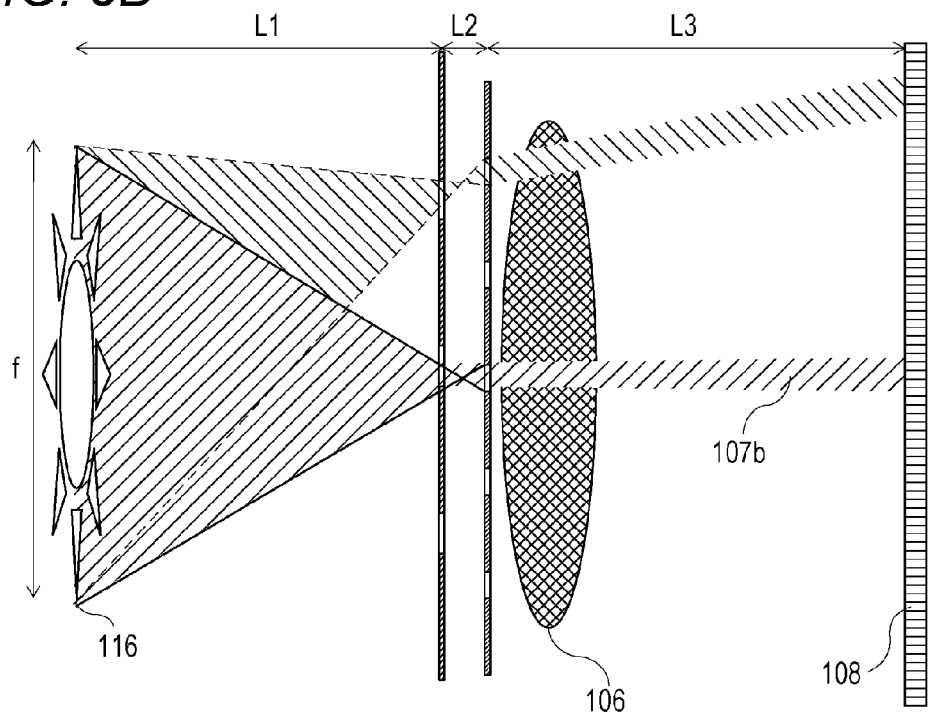

FIGS. 2, 3A, and 3B show schematic views illustrating a state where, in the present embodiment, the primary X-ray beams 104 divided by the first grating 103 enter the second grating 105, and are thereby formed into the secondary X-ray beams.

For giving a simple explanation of the present embodiment, only two primary X-ray beams, namely, the primary X-ray beams 104a and 104b are shown in FIGS. 2, 3A, and 3B. In the present embodiment, the other primary X-ray beams also enter the second grating 105 in the same manner as the two beams shown in FIGS. 2, 3A, and 3B.

In FIG. 2, the primary X-ray beam 104a passes through a transmitting portion 125a of the second grating and is thereby formed into the secondary X-ray beam 107a, and the primary X-ray beam 104b passes through a transmitting portion 125b of the second grating and is thereby formed into the secondary X-ray beam 107b. In FIG. 2, the primary X-ray beam 104a and the primary X-ray beam 104b which are adjacent to each other overlap on the front surface of the second grating 105. Both of an edge 124a of the primary X-ray beam 104a and an edge 124b of the primary X-ray beam 104b enter the same one of the blocking portions of the second grating 105. The edge of an X-ray beam indicates a portion that has at least a part of the contour of the X-ray beam in a plane parallel to the periodic direction of the grating. Further, the edges of the X-ray beams preferably enter the blocking portions in all planes that are perpendicular to the periodic direction of the grating.

Also in FIGS. 3A and 3B, in the same manner as shown in FIG. 2, the primary X-ray beam 104a passes through the transmitting portion 125a of the second grating and is thereby formed into the secondary X-ray beam 107a, and the primary X-ray beam 104b passes through the transmitting portion 125b and is thereby formed into the secondary X-ray beam 107b. Further, in the same manner as shown in FIG. 2, both of the edges of the two primary X-ray beams 104a and 104b enter the same one of the blocking portions of the second grating 105. In FIGS. 3A and 3B, a difference from FIG. 2 is that the adjacent primary X-ray beams 104a and 104b do not overlap on the front surface of the second grating 105, and there is therefore a gap therebetween. As shown in FIG. 3A, the adjacent primary X-ray beams 104a and 104b may respectively enter the adjacent transmitting portions 125a and 125b of the second grating 105. Alternatively, as shown in FIG. 3B, the adjacent primary X-ray beams 104a and 104b may enter respective transmitting portions of the second grating, the respective transmitting portions not being adjacent to each other.

Figure 4:
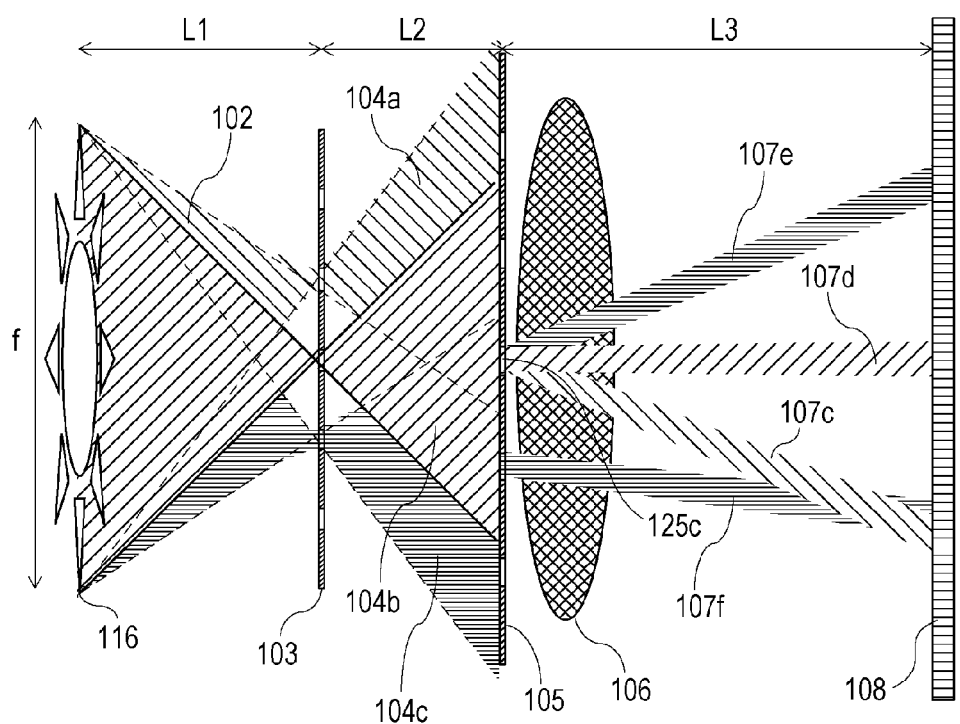
FIG. 4 is a schematic view of the positional relationship between an X-ray focal point and gratings according to a comparative example of the present invention.
Figure 5:
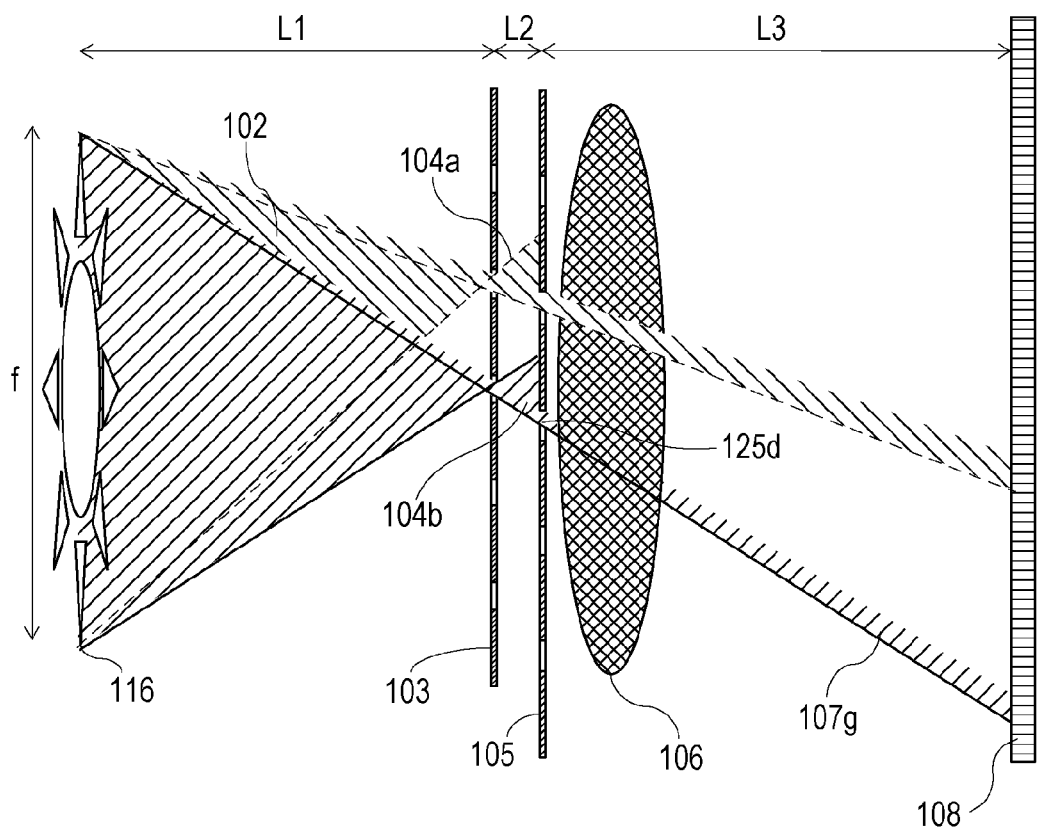
FIG. 5 is a schematic view of the positional relationship between an X-ray focal point and gratings according to a comparative example of the present invention.

Each of FIGS. 4 and 5 illustrates not the present embodiment, but a comparative example.

Also in each of FIGS. 4 and 5 illustrating a comparative example, only a part of the first grating, a part of the primary X-ray beams, and a part of the second grating are shown. The other regions that are not illustrated are the same as the illustrated region.

In FIG. 4, the primary X-ray beams 104a to 104c intersect each other on the front surface of the second grating 105. Further, each of the primary X-ray beams 104a to 104c extends across three of the transmitting portions of the second grating 105. The three primary X-ray beams 104a to 104c enter a transmitting portion 125c of the second grating 105. Therefore, the secondary X-ray beam 107c is formed from the primary X-ray beam 104a, the secondary X-ray beam 107d is formed from the primary X-ray beam 104b, and the secondary X-ray beam 107e is formed from the primary X-ray beam 104c.

In FIG. 5, the edges of the primary X-ray beams 104 are incident on the transmitting portions of the second grating 105.

In the state shown in each of FIGS. 2, 3A, and 3B, when the vibration of the position of the X-ray focal point 116 is within a specific range, it is possible to ignore the influence of the vibration of the X-ray focal point 116 and the scattering of the applied electrons on the secondary X-ray beams 107. The specific range referred to herein indicates a range by which, in the state shown in FIG. 2, the overlapping portion between the adjacent primary X-ray beams 104a and 104b on the front surface of the second grating 105 does not lie on any of the transmitting portions of the second grating 105. Further, in the state shown in each of FIGS. 3A and 3B, the edges of the respective primary X-ray beams do not enter any of the transmitting portions of the second grating 105.

Similarly, in the state shown in FIG. 4 as in the state shown in each of FIGS. 2, 3A, and 3B, when the vibration of the position of the X-ray focal point 116 is within a specific range, it is possible to ignore the influence of the vibration of the X-ray focal point 116 and the scattering of the applied electrons on the secondary X-ray beams 107. However, a plurality of secondary X-ray beams 107 (X-ray beams 107c to 107e, for example) are generated through one X-ray transmitting portion (the X-ray transmitting portion 125c, for example) of the second grating 105. When a plurality of secondary X-ray beams 107 are generated through one X-ray transmitting portion, the secondary X-ray beams 107 are prone to intersect or overlap each other between the second grating 105 and the detector 108 as the secondary X-ray beams 107c and 107f shown in FIG. 4. When the secondary X-ray beams intersect or overlap each other in this manner, positions on the specimen through which the respective secondary X-ray beams pass and positions on the detector where the respective secondary X-ray beams enter will become complicated. As a result, it becomes difficult to calculate information of the specimen. In particular, when the secondary X-ray beams 107c and 107f which have passed through respective different positions on the specimen overlap each other on the detector as shown in FIG. 4, it is difficult to obtain the amount of position deviation of each of the secondary X-ray beams (the position deviation being caused by the specimen). Therefore, information regarding a region on the specimen through which the secondary X-ray beam 107c has passed and information regarding a region on the specimen through which the secondary X-ray beam 107f has passed are mixed, thereby causing blurring on an image to be obtained.

On the other hand, in the state shown in FIG. 5, when the vibration of the X-ray focal point 116 occurs, the width of the secondary X-ray beam 107g which is emitted through the transmitting portion 125d of the second grating where the edge of the primary X-ray beam 104b enters changes. Therefore, it becomes difficult to calculate information of the specimen on the basis of a detection result obtained by the detector 108.

In a case where the edges of the respective primary X-ray beams 104 are incident on boundaries between the blocking portions and the transmitting portions of the second grating 105, when the X-ray focal point 116 vibrates so that the edges of the respective primary X-ray beams 104 move toward the blocking portions of the second grating 105, the width of each of the secondary X-ray beams does not change. Therefore, the edges of the primary X-ray beams 104 may be incident on the boundaries between the blocking portions and the transmitting portions of the second grating 105. Thus, in the present invention and the present specification, even when the edges of the respective plurality of primary X-ray beams 104 are incident on the boundaries between the blocking portions and the transmitting portions of the second grating 105, the edges of the respective plurality of primary X-ray beams 104 are regarded to be incident on the blocking portions of the second grating 105.

However, when taking into consideration irregular deviation of the vibration amount of the X-ray focal point and deviation in arrangement between the X-ray source, the first grating and the second grating, it is more preferred that the edges of the primary X-ray beams 104 enter the blocking portions of the second grating 105.

In view of the above, in the specimen information acquisition system of the present embodiment, the plurality of primary X-ray beams do not overlap each other on the transmitting portions of the second grating, and the edges of the respective plurality of primary X-ray beams enter the blocking portions of the second grating. This makes it possible to prevent the formation of a plurality of secondary X-ray beams through one transmitting portion of the second grating as shown in FIG. 4, and also prevent the change of the width of each of the secondary X-ray beams caused by the vibration of the X-ray focal point as shown in FIG. 5. In the case of the present embodiment using two-dimensional gratings, the plurality of primary X-ray beams do not overlap each other on the transmitting portions of the second grating in each of two periodic directions, and the edges of the respective plurality of primary X-ray beams enter the blocking portions of the second grating.

The conditions for the gratings for obtaining the above specimen information acquisition system will be described. The description will be made taking an example in which a one-dimensional grating having X-ray blocking portions and X-ray transmitting portions which are one-dimensionally arranged is used as each of the first grating and the second grating. When a one-dimensional grating is used as each of the first grating and the second grating, there are two conditions required for the first grating and the second grating. One of the conditions relates to arrangement positions of the first grating and the second grating in a z-axis direction which is along the optical axis. The other condition relates to arrangement positions of the first grating and the second grating in an x-axis direction. The x-axis indicates an axis along a direction corresponding to an alignment direction of each of the gratings on an x-y plane which is perpendicular to the z-axis. In this regard, the alignment direction of each of the gratings indicates an alignment direction of the X-ray transmitting portions and the X-ray blocking portions. Further, the direction corresponding to the alignment direction indicates a direction obtained by projecting the alignment direction of a grating on the x-y plane from the X-ray source side. That is, even when a grating is inclined with respect to the z-axis, the direction corresponding to the alignment direction of the grating lies on the x-y plane.

First, the condition for the arrangement positions of the first grating and the second grating in the z-axis direction will be described.

In the present embodiment, since one secondary X-ray beam 107 is formed from one primary X-ray beam 104 as shown in FIGS. 2, 3A, and 3B, the sum of the width of one transmitting portion and the width of one blocking portion of the first grating and the sum of the width of one transmitting portion and the width of one blocking portion of the second grating have the relationship expressed by the following formula (1).

[Expression 1]

$$Ga1 + Gb1 = \frac{L1}{L1+L2}(Ga2 + Gb2) \quad \text{formula (1)}$$

In the formula (1), the distance between the center of the X-ray focal point 116 and the center of the first grating 103 is denoted by L1, and the distance between the center of the first grating 103 and the center of the second grating 105 is denoted by L2. Further, the center indicates a center with respect to three directions in total including the optical axis direction, and two directions perpendicular to the optical direction.

Further, in the formula (1), a manufacturing error in each of the first grating and the second grating is not taken into consideration. In the present specification, in consideration of errors such as a fabrication error and an alignment error in each of the first grating and the second grating, the formula (1) is regarded to hold when the left side of the formula (1) is 0.95 to 1.05 times the right side thereof.

Further, in order to form one secondary X-ray beam 107 from one primary X-ray beam 104, it is necessary that the width of each of the primary X-ray beams 104 on the front surface of the second grating should be narrower than the sum of the width of one transmitting portion and twice the width of one blocking portion of the second grating 105. This is expressed by the following formula (2).

[Expression 2]

$$\frac{L2}{L1}(f + bf) + \frac{L1+L2}{L1}Ga1 \le Ga2 + 2Gb2 \quad \text{formula (2)}$$

In the formula (2), the size of the X-ray focal point in a direction that is parallel to the alignment direction of the transmitting portions and the blocking portions in the second dividing direction is denoted by f. Further, the length that is the sum of the vibration amount of the X-ray focal point and the length of two hems which are present at respective both sides of the X-ray focal point, the length being in the direction parallel to the alignment direction of the transmitting portions and the blocking portions in the second dividing direction, is denoted by df. If the X-ray focal point does not vibrate, df is only the length of the two hems. On the other hand, if the X-ray focal point does not have a hem, df is only the vibration amount thereof. Hereinafter, an expression such as "the length of the hem" indicates a length that is the sum of the length of two hems present at respective both sides of the X-ray focal point. Solving the formula (2) for L1 leads to the following formula (3).

[Expression 3]

$$\frac{f + df + Ga1}{Ga2 + 2Gb2 - Ga1}L2 \le L1 \quad \text{formula (3)}$$

The formula (3) expresses the condition for the arrangement positions of the first grating 103 and the second grating 105 in the z-axis. Upon the determination of an X-ray source (an X-ray focal point) to be used, and a first grating and a second grating to be used, values other than L1 and L2 can be assigned in the formula (3). Accordingly, L1 and L2 can be approximately determined on the basis thereof.

However, in the formula (3), the fabrication accuracy of each of the first grating and the second grating (the accuracy of Ga1, Gb1, Ga2 and Gb2), and the positional accuracy (the alignment accuracy) of each of the first grating and the second grating in the optical axis direction are not taken into consideration. That is, the formula (3) is not an exact formula. Therefore, in the formula (3), errors such as a fabrication error and an alignment error in each of the first grating and the second grating can be allowed.

In order to reduce the width of each of the secondary X-ray beams 107 on the detector, it is preferred to determine L1 and L2 so that the value of the left side of the formula (3) comes close to the value of the right side thereof. Further, it is more preferred to determine L1 and L2 so that the value of the left side of the formula (3) becomes equal to the value of the right side thereof. The reason thereof will be described below.

The width (Bs) of each of the secondary X-ray beams 107 on the detector 108 when using the first grating 103 and the second grating 105 is expressed by the following formula (4).

[Expression 4]

$$Bs = Ga2 + \frac{L3}{L2}(Ga1 + Ga2) \quad \text{formula (4)}$$

In the formula (4), the distance between the center of the second grating 105 and the center of a detection surface of the detector 108 is denoted by L3. In the present specification, the detection surface of the detector indicates only a region where the x-ray beams enter in the surface of the detector 108.

It can be seen from the formula (4) that in order to reduce the width of each of the secondary X-ray beams 107 on the detector 108, it is necessary to reduce the width of each of the X-ray transmitting portions of each of the first grating 103 and the second grating 105 (Ga1, Ga2), make L3 smaller, and make L2 larger.

It can be seen from the above that in order to reduce the width of each of the secondary X-ray beams 107 on the detector 108, it is preferred to determine L1 and L2 so that the values of both sides of the formula (3) come close to each other, and it is more preferred to determine L1 and L2 so that the values of both sides of the formula (3) become equal to each other. However, regardless of the difference between the values of both sides of the formula (3), it is possible to satisfy the condition for the arrangement positions of the first grating and the second grating in the z-axis direction by determining L1 and L2 so as to satisfy the formula (3).

Figure 6A:
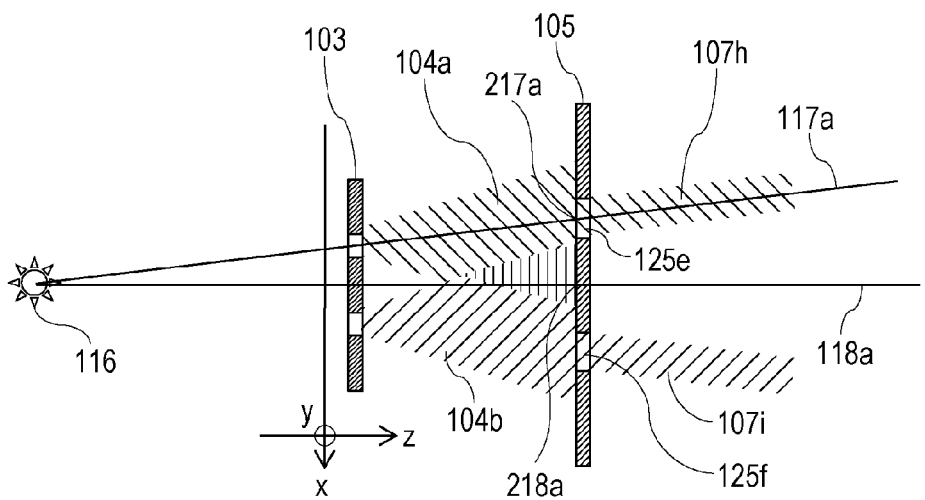
FIGS. 6A and 6B are enlarged views of the positional relationship between the X-ray focal point and the gratings according to the first embodiment of the present invention.
Figure 6B:
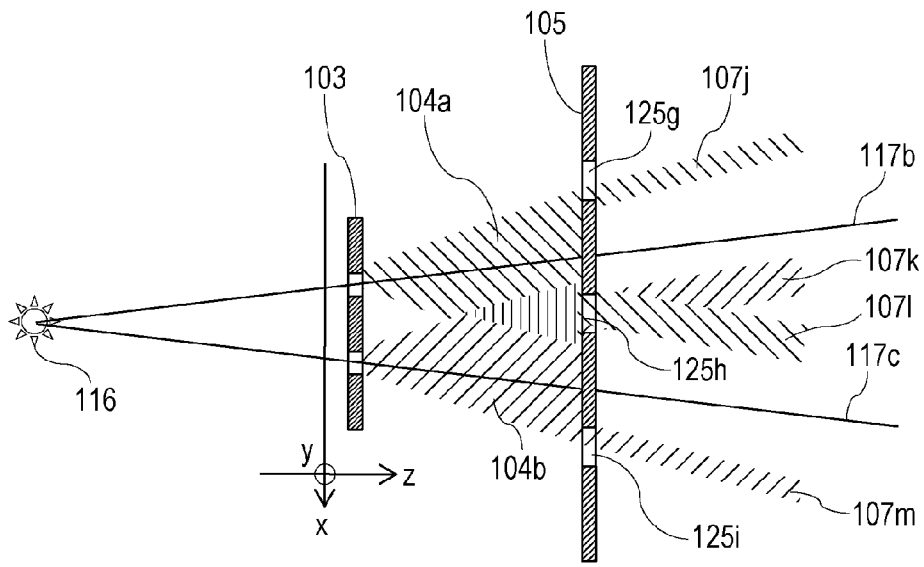

Next, the condition for the arrangement positions of the first grating and the second grating in the x-axis direction will be described. FIGS. 6A and 6B are enlarged views of adjacent ones of the primary X-ray beams 104 and the second grating 105 when the adjacent primary X-ray beams 104 overlap each other on the second grating 105 as shown in FIG. 2. In FIGS. 6A and 6B, the horizontal direction corresponds to the z-axis (the optical axis) and the vertical direction corresponds to the x-axis. Further, the depth direction with respect to the sheet corresponds to the y-axis.

As shown in FIG. 6A, when the first grating and the second grating are arranged so that the adjacent primary X-ray beams overlap each other on one of the blocking portions of the second grating 105, one secondary X-ray beam 107h is emitted through one transmitting portion 125e of the second grating 105. On the other hand, as shown in FIG. 6B, when the first grating and the second grating are arranged so that the adjacent primary X-ray beams overlap each other on one of the transmitting portions of the second grating 105, two secondary X-ray beams 107k and 107l are emitted through one transmitting portion 125h of the second grating. When a plurality of secondary X-ray beams are emitted through one transmitting portion in this manner, the secondary X-ray beams are prone to intersect or overlap each other between the second grating 105 and the detector 108 as is the case of the comparative example shown in FIG. 4. Therefore, such arrangement is not desirable.

Thus, it is necessary to arrange the first grating and the second grating so that adjacent ones of the primary X-ray beams do not overlap each other on any of the transmitting portions of the second grating, which includes not only the case where adjacent ones of the primary X-ray beams do not overlap each other as shown in FIG. 3, but also the case where adjacent ones of the primary X-ray beams overlap each other on the second grating only at the blocking portions thereof as shown in FIG. 6A. In order to arrange the first grating and the second grating in this manner, the arrangement positions of the first grating and the second grating are required to satisfy at least one of two conditions described below in the x-axis direction.

A first condition is that the center of the X-ray focal point 116, the center of one of the transmitting portions of the first grating 103, and the center of one of the transmitting portions of the second grating 105 substantially lie on a single straight line 117a. A second condition is that the center of the X-ray focal point 116, the center of one of the blocking portions of the first grating 103, and the center of one of the blocking portions of the second grating 105 substantially lie on a single straight line 118a. The term "substantially" means that an error dx described below is allowed. Therefore, on the basis of the arrangement in which the transmitting portion or the blocking portion of the second grating lie on the two straight lines, the maximum error in the x-axis direction which is allowed for the second grating 105 with respect to the straight line 117a or the straight line 118a will be considered. The allowable maximum error is a value that is calculated by subtracting the width of one primary x-ray beam on the second grating from the sum of the width of one transmitting portion of the second grating and twice the width of one blocking portion thereof. Therefore, the allowable maximum error dx in the x-axis direction is expressed by the following formula (5).

[Expression 5]

$$dx = \frac{1}{2}\left(Ga2 + 2Gb2 - \frac{L2}{L1}(f + df + Ga1) - Ga1\right)$$ formula (5)

In other words, the first condition described above is that the distance between an intersecting point 217a of the straight line 117a passing through the center of the X-ray focal point and the center of one of the transmitting portions of the first grating with the front surface of the second grating and the center of one of the transmitting portions of the second grating, the one being closest to the intersecting point 217a, is smaller than dx expressed by the formula (5). Further, the second condition described above is that the distance between an intersecting point 218a of the straight line 118a passing through the center of the X-ray focal point and the center of one of the blocking portions of the first grating with the front surface of the second grating and the center of one of the blocking portions of the second grating, the one being closest to the intersecting point 218a, is smaller than dx expressed by the formula (5).

Further, the first grating is moved by the first moving unit as the first moving means. Similarly, the second grating is moved by the second moving unit as the second moving means. Each of the first moving unit and the second moving unit has an actuator, allows each of the first grating and the second grating to perform one or both of parallel movement and rotational movement, and performs alignment for each of the first grating and the second grating. The rotational movement includes rotational movement on the x-y plane, namely, movement of inclination (tilt) with respect to the optical axis.

The secondary X-ray beams 107 which have passed through the specimen 106 are detected by the detector 108. In the present embodiment, the detector 108 is a two-dimensional detector having two-dimensionally arranged image pickup devices and can take an X-ray image. For example, a flat panel detector (FPD) and a charge coupled device (CCD) both of which are capable of converting an X-ray beam into a digital signal can be used as the detector 108.

A detection result obtained by the detector 108 is transferred to the calculator 114, and the calculator 114 then performs calculation, thereby obtaining information of the specimen. The information of the specimen indicates, for example, information that can become the basis for a phase image, a differential phase contrast image and a scattering image (a visibility image) of the specimen, and the phase image, the differential phase contrast image and the scattering image (a visibility image) of the specimen can be acquired by mapping the information. Since the detection result itself obtained by the detector also includes information of the specimen, the detection result is also regarded as one type of information of the specimen in the present invention and the present specification. The calculator 114 may be prepared separately from the specimen information acquisition system, and connected to the detector to thereby perform a calculation for acquiring information regarding the phase of the specimen. Further, as necessary, the specimen information acquisition system may be provided with a display device (not shown) which displays information regarding the phase of the specimen acquired by the calculation performed by the calculator 114, and an image obtained by mapping the information.

Hereinabove, the present embodiment has been described taking the example in which two one-dimensional gratings are used. However, two-dimensional gratings each having X-ray transmitting portions and X-ray blocking portions which are two-dimensionally arranged may be used instead of the one-dimensional gratings, or two or more gratings may be used. Also when two or more gratings are used, beams that enter the detector are defined as secondary X-ray beams. For example, when three gratings are used, one of the three gratings, the one being closest to the X-ray source, is defined as a zeroth grating, and X-ray beams that are formed by the zeroth grating are defined as zero-order X-ray beams. Further, a grating that divides the zero-order X-ray beams is defined as a first grating, and X-ray beams that are formed by the first grating are defined as primary X-ray beams. Further, a grating that divides the primary X-ray beams is defined as a second grating, and X-ray beams formed by the second grating are defined as secondary X-ray beams. Accordingly, the secondary X-ray beams enter the detector.

In the present embodiment, X-rays that are formed into the secondary X-ray beams 107 incident on the detector 108 are emitted from a part of the X-ray focal point 116. Therefore, it is possible to reduce the influence of the vibration of the X-ray focal point 116 and the scattering of the applied electrons on the secondary X-ray beams 107.

By using the specimen information acquisition system of the present embodiment, although depending on the width of each of the transmitting portions and the width of each of the blocking portions of each of the first grating and the second grating, an approximately 2 m×1 m of imaging field can be obtained.

(Second Embodiment)

FIGS. 7A, 7B, 8A, and 8B are schematic views illustrating a state where primary X-ray beams enter a second grating, and are thereby formed into secondary X-ray beams in a specimen information acquisition system according to a second embodiment. The specimen information acquisition system of the present embodiment differs from the specimen information acquisition system of the first embodiment in that a plurality of secondary X-ray beams are formed from one primary X-ray beam. Therefore, the width of each of X-ray transmitting portions and the width of each of X-ray blocking portions of each of first and second gratings, and the arrangement of the first and second gratings in the present embodiment differ from those in the first embodiment. The other configurations are the same as those of the specimen information acquisition system of the first embodiment. Further, in FIGS. 7A, 7B, 8A, and 8B, the secondary X-ray beams are not shown.

As described above, in the specimen information acquisition system of the present embodiment, a plurality of secondary X-ray beams are formed from one primary X-ray beam. However, as is the case of the specimen information acquisition system of the first embodiment, a plurality of primary X-ray beams do not overlap each other on the X-ray transmitting portions of the second grating, and edges of the respective primary X-ray beams enter the X-ray blocking portions of the second grating. However, since a plurality of secondary X-ray beams are formed from one primary X-ray beam, the above formula (1) does not hold. Accordingly, there are some different points in the condition in the z-axis direction and the condition in the x-axis direction between the specimen information acquisition system of the present embodiment and the specimen information acquisition system of the first embodiment. Therefore, the different points will be described below.

Figure 9A:
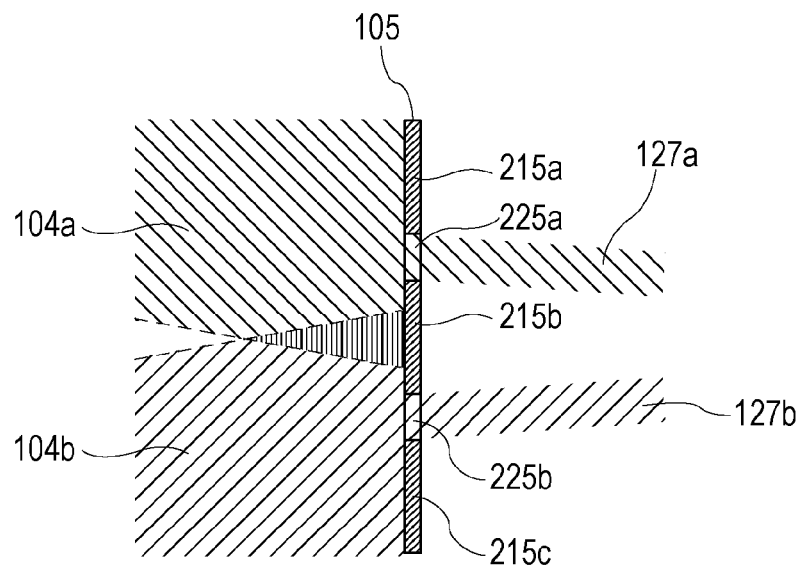
FIGS. 9A and 9B are enlarged views of the positional relationship between an X-ray focal point and gratings according to the second embodiment of the present invention.
Figure 9B:
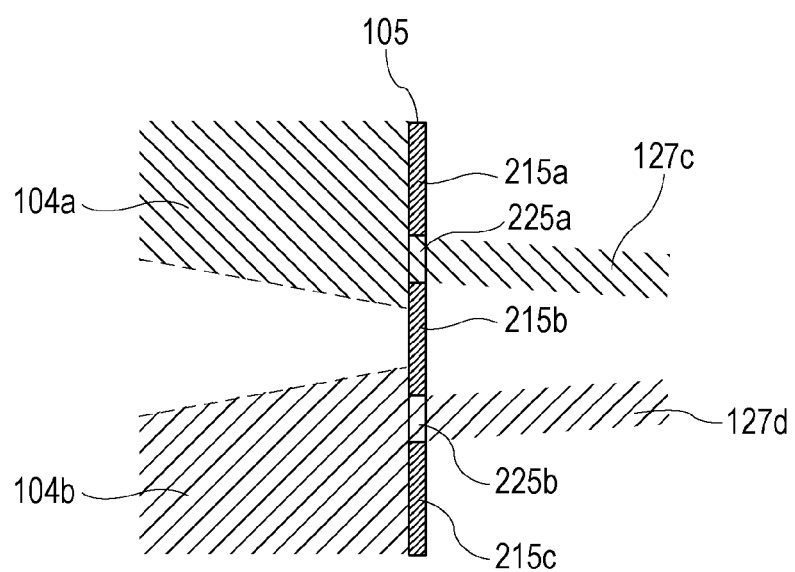

FIGS. 9A and 9B are enlarged views illustrating a state where adjacent primary X-ray beams 104a and 104b are incident on the second grating 105 in the present embodiment.

FIG. 9A corresponds to FIG. 2 of the first embodiment, and is an enlarged view of FIG. 7 in an overlapping portion between the adjacent primary X-ray beams 104a and 104b on the second grating. FIG. 9A illustrates a state where the edges of the respective adjacent primary X-ray beams 104a and 104b enter one blocking portion 215b of the second grating, and a secondary X-ray beams 127a and 127b are thereby formed.

FIG. 9B corresponds to FIG. 3A of the first embodiment, and is an enlarged view of FIG. 8 in a gap between the adjacent primary X-ray beams 104a and 104b on the second grating. FIG. 9B illustrates a state where the adjacent primary X-ray beams 104a and 104b do not overlap each other, and the edges of the respective primary X-ray beams 104a and 104b enter the one blocking portion 215b and a secondary X-ray beams 127c and 127d are thereby formed.

Figure 10A:
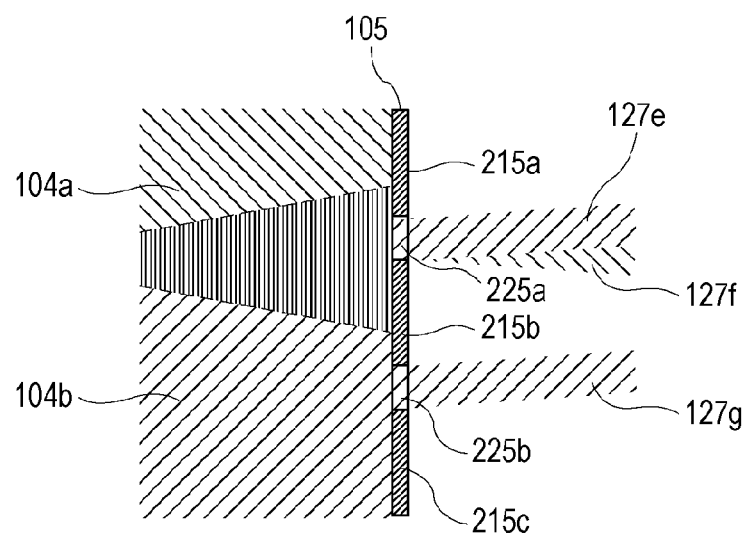
FIGS. 10A and 10B are enlarged views of the positional relationship between the X-ray focal point and the gratings according to the comparative examples of the present invention.
Figure 10B:
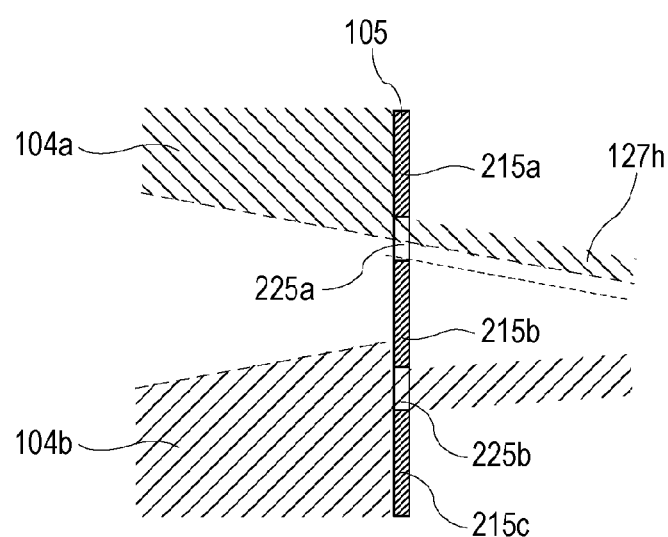

FIGS. 10A and 10B are enlarged views illustrating a state where the adjacent primary X-ray beams 104a and 104b are incident on the second grating 105 in comparative examples.

FIG. 10A corresponds to the comparative example shown in FIG. 4. That is, FIG. 10A illustrates a state where the adjacent primary X-ray beams 104a and 104b overlap each other on the second grating, and the edge of the primary X-ray beam 104a and the edge of the primary x-ray beam 104b enter a blocking portion 215c and a blocking portion 215a of the second grating, respectively. Therefore, the primary X-ray beams 104a and 104b overlap each other on a transmitting portion 225a of the second grating, and two secondary X-ray beams 127e and 127f are formed through the transmitting portion 225a.

When a plurality of secondary X-ray beams are formed through one transmitting portion of the second grating in this manner, the same problems as those in the comparative example shown in FIG. 4 are prone to occur. More specifically, the secondary X-ray beams are prone to intersect or overlap each other between the second grating and the detector. As a result, it becomes difficult to calculate information of the specimen, and blurring is likely to be generated in an obtained image. Further, depending on the incident angle of each of the primary X-ray beams, two secondary X-ray beams partially overlap each other, and a secondary X-ray beam having a larger width than a secondary X-ray beam 127g which is formed from the one primary X-ray beam 104b may thereby be formed. When there are variations in width among the plurality of secondary X-ray beams formed by the second grating in this manner, it becomes difficult to calculate information of the specimen on the basis of the detection result.

FIG. 10B corresponds to the comparative example shown in FIG. 5. More specifically, FIG. 10B illustrates a state where the adjacent primary X-ray beams 104a and 104b do not overlap each other on the second grating, and the edge of the primary X-ray beam 104a enters the transmitting portion 225a of the second grating.

When the edge of a primary X-ray beam enters a transmitting portion of the second grating in this manner, the same problem as that in the comparative example shown in FIG. 5 is prone to occur. More specifically, when the vibration of the X-ray focal point 116 occurs, the width of the secondary X-ray beam 127h which is emitted through the transmitting portion 225a of the second grating where the edge of the primary X-ray beam 104a enters changes, thereby making it difficult to calculate information of the specimen on the basis of the detection result obtained by the detector 108.

In view of the above, as with the case of the specimen information acquisition system of the first embodiment, the plurality of primary X-ray beams do not overlap each other on the transmitting portions of the second grating, and the edges of the respective primary X-ray beams enter the blocking portions of the second grating also in the specimen information acquisition system of the present embodiment. This makes it possible to prevent the formation of a plurality of secondary X-ray beams through one transmitting portion of the second grating, and also prevent the change of the width of each of the secondary X-ray beams caused by the vibration of the X-ray focal point. Therefore, it is possible to reduce the influence of the vibration of the X-ray focal point 116 and the scattering of the applied electrons on the secondary X-ray beams.

The conditions for the gratings for obtaining the above specimen information acquisition system will be described. The description will be made taking an example in which a one-dimensional grating having X-ray blocking portions and X-ray transmitting portions which are one-dimensionally arranged is used as each of the first grating and the second grating also in the present embodiment. Also in the present embodiment, two conditions including a condition relating to the arrangement positions of the first grating and the second grating in the z-axis direction and a condition relating to the arrangement positions of the first grating and the second grating in the x-axis direction are required.

First, the condition for the arrangement positions of the first grating and the second grating in the z-axis direction will be described. When one secondary X-ray beam is formed from one primary X-ray beam as in the first embodiment, even when there is a transmitting portion where no primary X-ray beam enters in the second grating as shown in FIG. 3B, a substantially constant pitch between the secondary X-ray beams can be achieved. However, when a plurality of secondary X-ray beams are formed from one primary X-ray beam as in the present embodiment, if there is a transmitting portion where no primary X-ray beam enters, a secondary X-ray beam on such a region will be defect. Therefore, information of the specimen cannot be acquired on the region in which a secondary X-ray beam is defect. As a result, the information of the specimen will be partially missing. A part of the information on the region in which a secondary X-ray beam is defect can be acquired by scanning the specimen. However, in such a case, scanning means may be required for the scanning, imaging time may be increased, and radiation exposure may be increased. Therefore, less defect of secondary X-ray beams is preferred. In order to prevent the defect of a secondary X-ray beam, it is necessary that a gap between adjacent ones of the primary X-ray beams on the second grating be smaller than the width of each of the blocking portions of the second grating. On the other hand, in order to allow only one primary X-ray beam to enter one transmitting portion of the second grating, it is necessary that the width of an overlapping portion between adjacent ones of the primary X-ray beams on the second grating be smaller than the width of each of the blocking portions of the second grating.

Allowing only one primary X-ray beam to enter one transmitting portion of the second grating while preventing the defect of a secondary X-ray beam is the same as allowing the edges of adjacent ones of the primary X-ray beams enter one blocking portion of the second grating. The edges of the adjacent primary X-ray beams indicate edges that are closer to each other in the alignment direction thereof. For example, in FIG. 8A, the edges indicate one of edges of the primary X-ray beam 104a, the one being located at the side of the primary X-ray beam 104b (the lower side when the alignment direction is the vertical direction in FIG. 8A) and one of edges of the primary X-ray beam 104b, the one being located at the side of the primary X-ray beam 104a (the upper side).

The condition for allowing only one primary X-ray beam to enter one transmitting portion of the second grating while preventing the defect of a secondary X-ray beam is expressed using the following formulae.

The condition for allowing adjacent ones of the primary X-ray beams to be in contact with each other on the second grating 105 is expressed by the following formula (6).

[Expression 6]

$$\frac{L1+L2}{L1}(Ga1+Gb1) = \frac{L2}{L1}(f+df) + \frac{L1+L2}{L1}Ga1 \quad \text{formula (6)}$$

The left side of the formula (6) is the length of a pair of one transmitting portion and one blocking portion of the first grating projected on the second grating, namely, the length of a pitch of the first grating projected on the second grating when the size of a light source (f+df) is an infinitesimal. On the other hand, the right side of the formula (6) is the width of each of the primary X-ray beams on the front surface of the second grating when the size of the right source is f+df.

When adjacent ones of the primary X-ray beams overlap each other on the second grating, the following formula (7) holds.

[Expression 7]

$$\frac{L1+L2}{L1}(Ga1+Gb1) \leq \frac{L2}{L1}(f+df) + \frac{L1+L2}{L1}Ga1 \quad \text{formula (7)}$$

In order to allow only one primary X-ray beam to enter one transmitting portion of the second grating, it is necessary that the width of an overlapping portion between adjacent ones of the primary X-ray beams on the front surface of the second grating be smaller than the width of each of the blocking portions of the second grating. This condition leads to the following formula (8).

[Expression 8]

$$\frac{L1+L2}{L1}(Ga1+Gb1) - Gb2 \leq \frac{L2}{L1}(f+df) + \frac{L1+L2}{L1}Ga1 \quad \text{formula (8)}$$

Upon the determination of a first grating and a second grating to be used in the specimen information acquisition system, it is possible to determine the arrangement positions of the first grating and the second grating in the z-axis direction by appropriately determining L1 and L2 so as to satisfy the formula (8).

Next, when adjacent ones of the primary X-ray beams are spaced from each other on the front surface of the second grating, the following formula (9) holds.

[Expression 9]

$$\frac{L1+L2}{L1}(Ga1+Gb1) > \frac{L2}{L1}(f+df) + \frac{L1+L2}{L1}Ga1 \quad \text{formula (9)}$$

Similarly, in order to prevent the defect of a secondary X-ray beam even when adjacent ones of the primary X-ray beams are spaced from each other on the front surface of the second grating, it is necessary that a gap between the adjacent primary x-ray beams on the second grating be smaller than the width of each of the blocking portions of the second grating.

This condition leads to following formula (10).

[Expression 10]

$$\frac{L2}{L1}(f+df) + \frac{L1+L2}{L1}Ga1 \le \frac{L1+L2}{L1}(Ga1+Gb1) + Ga2 \quad \text{formula (10)}$$

By appropriately determining L1 and L2 so as to satisfy the formula (8) and the formula (10), it is possible to determine the arrangement positions of the first grating and the second grating in the z-axis direction.

Further, a design value of the first grating 103 suitable for a specific second grating 105 can be obtained from the formula (8). For example, the width Gb1 of each of the blocking portions of the first grating 103 can be determined by using the following formula (11) which is a modification of the formula (8).

[Expression 11]

$$Gb1 \le \frac{L2}{L1+L2}(f+df) + \frac{L1}{L1+L2}Gb2 \quad \text{formula (11)}$$

The design value of the first grating 103 suitable for a specific second grating 105 can also be obtained from the formula (10). For example, the width Gb1 of each of the blocking portions of the first grating 103 can be determined by using the following formula (12) which is a modification of the formula (10).

[Expression 12]

$$Gb1 \ge \frac{L2}{L1+L2}(f+df) - \frac{L1}{L1+L2}Gb2 \quad \text{formula (12)}$$

Further, the following formula (13) which calculates the width Gb1 of each of the blocking portions of the first grating 103 suitable for a specific second grating 105 can be obtained on the basis of the formula (11) and the formula (12).

[Expression 13]

$$\frac{L2}{L1+L2}(f+df) - \frac{L1}{L1+L2}Gb2 \le \quad \text{formula (13)}$$
$$Gb1 \le \frac{L2}{L1+L2}(f+df) + \frac{L1}{L1+L2}Gb2$$

By determining the width (Gb1, Gb2) of the respective blocking portions of the first grating and the second grating and the arrangement positions (L1, L2) of the first grating and the second grating so as to satisfy the formula (13), the edges of adjacent ones of the primary X-ray beams can enter one blocking portion of the second grating as shown in FIG. 9.

Next, the condition for the arrangement positions of the first grating and the second grating in the x-axis direction will be described. The condition for the arrangement positions of the first grating and the second grating in the x-axis direction differs between a case where adjacent ones of the primary X-ray beams overlap each other on the second grating and a case where adjacent ones of the X-ray beams do not overlap each other one the second grating.

First, the case where adjacent ones of the primary X-ray beams overlap each other on the second grating will be described. As is the case of the first embodiment, when a transmitting portion of the second grating is located at a position where adjacent primary X-ray beams overlap each other on the second grating, two secondary X-ray beams are generated through the transmitting portion. In order to prevent such a situation to allow only one primary X-ray beam to enter one transmitting portion of the second grating, it is necessary that the arrangement positions of the first grating and the second grating satisfy at least one of two conditions described below in the x-axis direction.

Figure 7A:
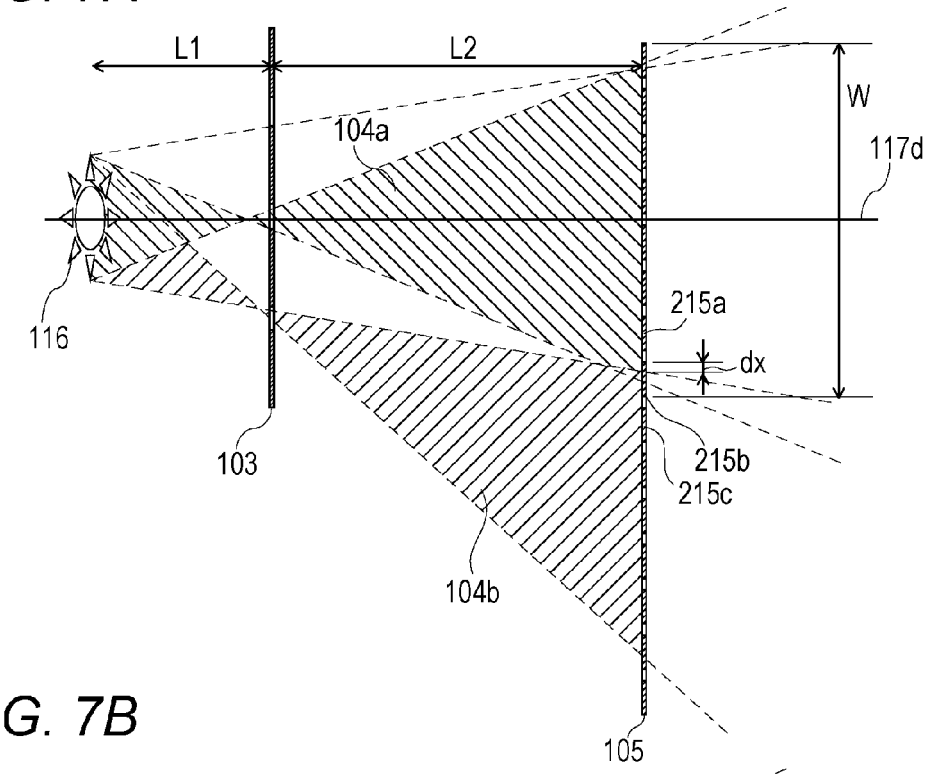
FIGS. 7A and 7B are schematic views of a specimen information acquisition system according to a second embodiment of the present invention.
Figure 7B:
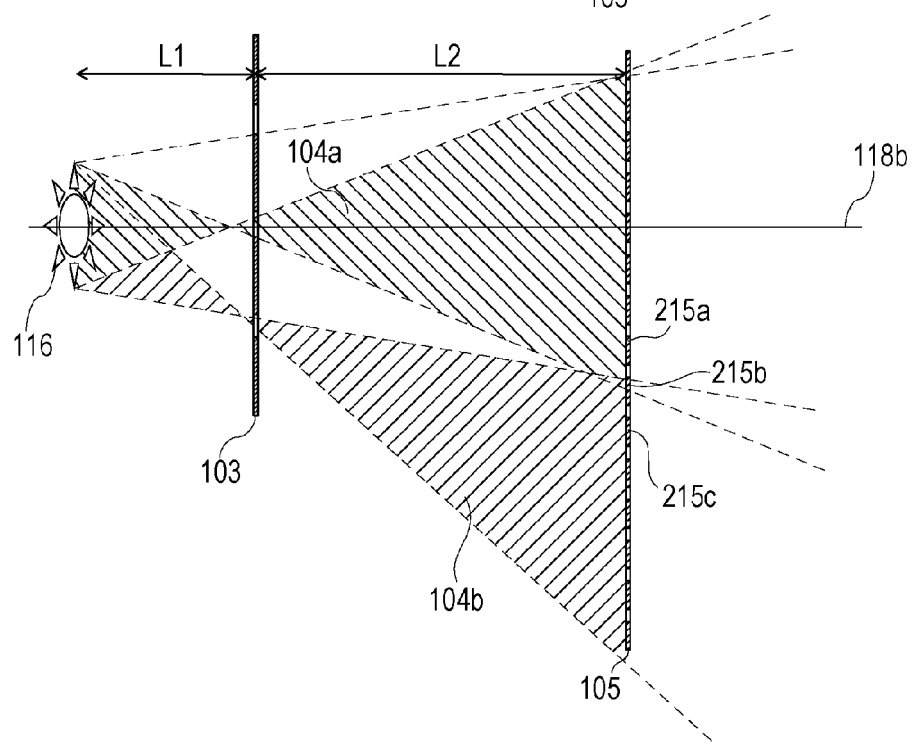

A first condition is that the center of the X-ray focal point 116, the center of one of the transmitting portions of the first grating 103, and the center of one of the transmitting portions of the second grating 105 lie on a straight line 117d (FIG. 7A). A second condition is that the center of the X-ray focal point 116, the center of one of the transmitting portions of the first grating 103, and the center of one of the blocking portions of the second grating 105 lie on a straight line 118b (FIG. 7B).

On the basis of the arrangement in which the transmitting portion or the blocking portion of the second grating lie on the two straight lines, the maximum error in the x-axis direction which is allowed for the second grating 105 with respect to the straight line 117d or the straight line 118b will be considered. As shown in FIG. 7A, the allowable maximum error dx is a value that is a half of the difference between the sum of the integral multiple of the width of a pair of one transmitting portion and one blocking portion of the second grating and the width of one blocking portion of the second grating ("W" in FIG. 7A) and the width of one primary x-ray beam on the front surface of the second grating. Therefore, dx is expressed by the following formula (14).

[Expression 14]

$$dx = \frac{1}{2}\left((Ga2+Gb2) \times m + Gb2 - \frac{L2}{L1}(f+df+Ga1) - Ga1\right) \quad \text{formula (14)}$$

In this regard, m is a minimum integer that satisfies the following formula (15).

[Expression 15]

$$m \ge \frac{\frac{L2}{L1}(f+df+Ga1) + Ga1 - Gb2}{Ga2+Gb2} \quad \text{formula (15)}$$

In FIG. 7A, m=7. In the first embodiment, m=1.

In other words, the first condition described above is that the distance between a straight line that passes through the center of the X-ray focal point and the center of one of the transmitting portions of the first grating and the center of one of the transmitting portions of the second grating is smaller than dx expressed by the formula (14). Further, the second condition described above is that the distance between a straight line that passes through the center of the X-ray focal point and the center of one of the transmitting portions of the first grating and the center of one of the blocking portions of the second grating is smaller than dx expressed by the formula (14).

However, as is the case of the first embodiment, the fabrication accuracy of each of the first grating and the second grating (Ga1, Gb1, Ga2 and Gb2) and the positional accuracy (the alignment accuracy) of each of the first grating and the second grating in the optical axis direction are not taken into consideration in the formula (13) and the formula (14). That is, each of the formula (13) and the formula (14) is not an exact formula. Therefore, errors such as a fabrication error and an alignment error in each of the first grating and the second grating can be allowed.

Next, the case where adjacent ones of the primary X-ray beams do not overlap each other on the second grating will be described. When a transmitting portion of the second grating is located at a position where no primary X-ray beam enters, no secondary X-ray beam is formed through the transmitting portion. When there is a transmitting portion of the second grating through which no secondary X-ray beam is formed, information of the specimen may be missing.

In order to prevent such a situation, it is necessary that the arrangement positions of the first grating and the second grating satisfy at least one of two conditions described below in the x-axis direction.

Figure 8A:
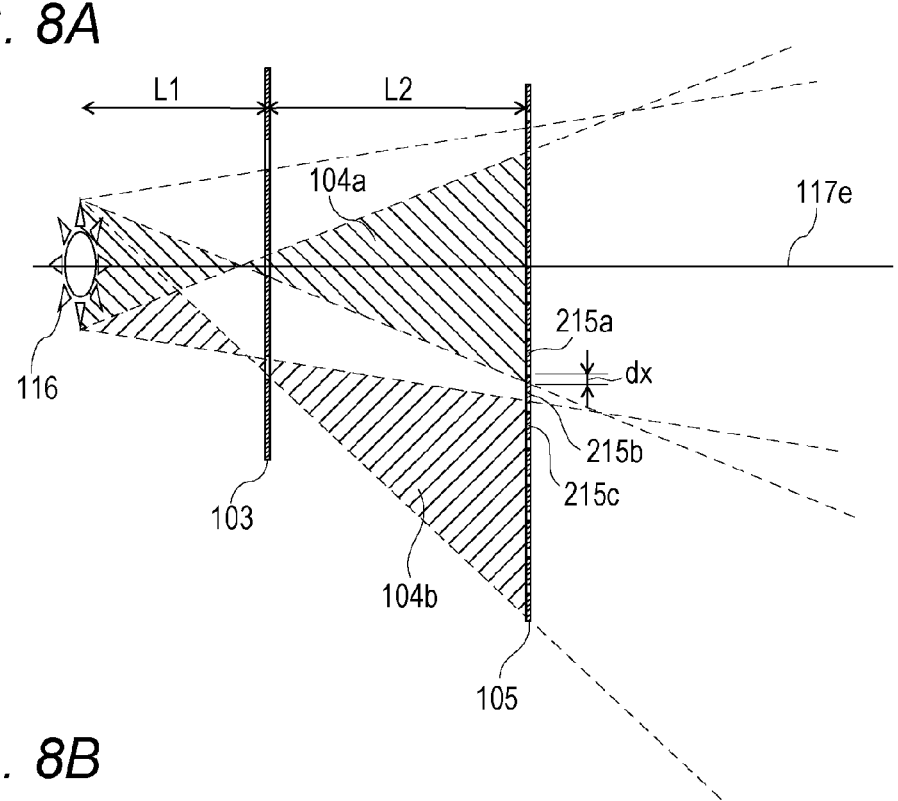
FIGS. 8A and 8B are schematic views of the specimen information acquisition system according to the second embodiment of the present invention.
Figure 8B:
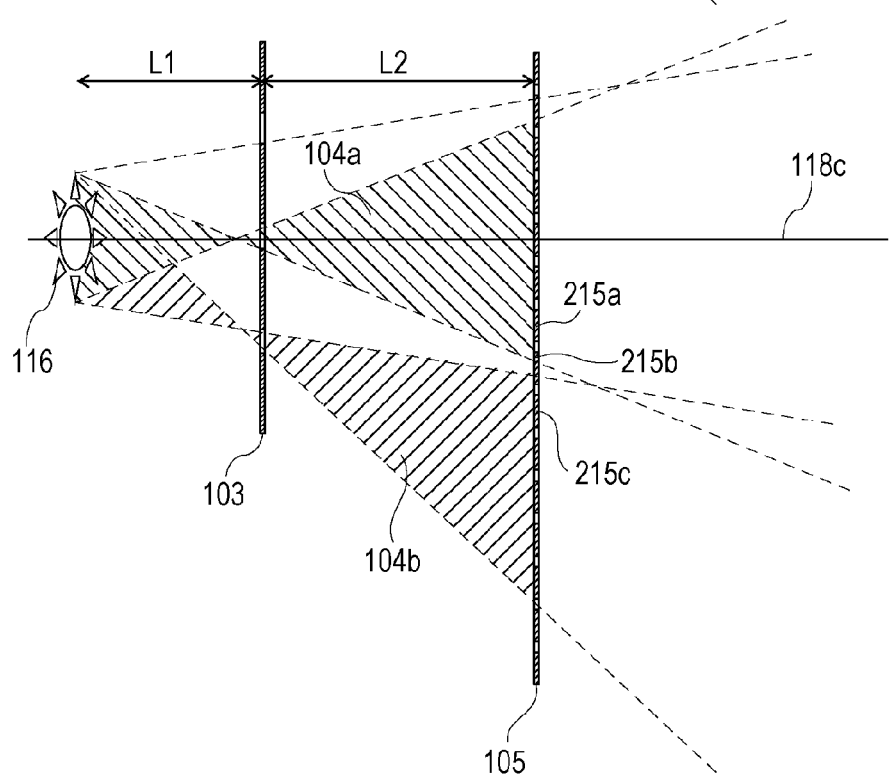

A first condition is that the center of the X-ray focal point 116, the center of one of the transmitting portions of the first grating 103, and the center of one of the transmitting portions of the second grating 105 lie on a straight line 117e (FIG. 8A). A second condition is that the center of the X-ray focal point 116, the center of one of the transmitting portions of the first grating 103, and the center of one of the blocking portions of the second grating 105 lie on a straight line 118c (FIG. 8B).

On the basis of the arrangement in which the transmitting portion or the blocking portion of the second grating lie on the two straight lines, the maximum error in the x-axis direction which is allowed for the second grating 105 with respect to the straight line 117e or the straight line 118c will be considered.

As shown in FIG. 8A, the allowable maximum error dx is a value that is a half of the difference between the sum of the integral multiple of the width of a pair of one transmitting portion and one blocking portion of the second grating and the width of one transmitting portion of the second grating and the width of one primary X-ray beam on the front surface of the second grating. Therefore, dx is expressed by the following formula (16).

[Expression 16]

$$dx = \frac{1}{2}\left(\frac{L2}{L1}(f + df + Ga1) + Ga1 - (Ga2 + Gb2) \times n - Gb2\right) \quad \text{formula (16)}$$

In this regard, n is a maximum integer that satisfies the following formula (17).

[Expression 17]

$$n \leq \frac{\frac{L2}{L1}(f + df + Ga1) + Ga1 - Gb2}{Ga2 + Gb2} \quad \text{formula (17)}$$

In other words, the first condition described above is that the distance between a straight line that passes through the center of the X-ray focal point and the center of one of the transmitting portions of the first grating and the center of one of the transmitting portions of the second grating is smaller than dx expressed by the formula (16). Further, the second condition described above is that the distance between a straight line that passes through the center of the X-ray focal point and the center of one of the transmitting portions of the first grating and the center of one of the blocking portions of the second grating is smaller than dx expressed by the formula (16).

However, as is the case of the first embodiment, the fabrication accuracy of each of the first grating and the second grating (Ga1, Gb1, Ga2 and Gb2) and the positional accuracy of each of the first grating and the second grating in the optical axis direction are not taken into consideration in the formula (16). That is, the formula (16) is not an exact formula. Therefore, errors such as a fabrication error and an alignment error in each of the first grating and the second grating can be allowed.

A larger allowable value for the arrangement error of each of the first grating 103 and the second grating 105 in the x-axis direction gives advantage to the system design. When the formula (6) which expresses the condition for allowing adjacent ones of the primary X-ray beams 104 to be in contact with each other on the second grating 105 is satisfied, the allowable value for the arrangement error of each of the first grating 103 and the second grating 105 in the x-axis direction becomes maximum. In the present specification, in consideration of a manufacturing error in each of the first grating and the second grating, the formula (6) is regarded to hold when the left side of the formula (6) is 0.95 to 1 times the right side thereof.

Hereinabove, the present embodiment has been described taking an example in which two one-dimensional gratings are used. However, two-dimensional gratings each having X-ray transmitting portions and X-ray blocking portions which are two-dimensionally arranged may be used instead of the one-dimensional gratings, or two or more gratings may be used. Also in the present embodiment, X-rays that are formed into the secondary X-ray beams 107 incident on the detector 108 are emitted from a part of the X-ray focal point, the part being close to the center thereof as in the first embodiment. Therefore, it is possible to reduce the influence of the vibration of the X-ray focal point 116 and the scattering of the applied electrons on the secondary X-ray beams 107.

By using the specimen information acquisition system of the present embodiment, although depending on the width of each of the transmitting portions and the width of each of the blocking portions of each of the first grating and the second grating, an approximately 2 m×1 m of imaging field can be obtained.

[First Exemplary Embodiment]

In a first exemplary embodiment, a more specific embodiment than the first embodiment will be described.

In the present exemplary embodiment, the basic configuration of the specimen information acquisition system is the same as that shown in FIG. 1.

In the present exemplary embodiment, a rotating anticathode type X-ray source with a molybdenum, silver or tungsten target is used as the X-ray source. The size of the effective focal point is 300 μm, the vibration amount of the X-ray focal point is 5 μm, and the width of the hem of the X-ray focal point is 150 μm. Divergent X-rays are generated from the X-ray source, and directed to the first grating and the second grating.

In the first grating, the width of each of transmitting portions is 30 μm. In the second grating, transmitting portions each of which has a width of 60 μm and blocking portions each of which has a width of 140 μm are aligned. The focusing position is located at a position 80 cm away from the second grating. When the distance between the X-ray focal point and the second grating is 80 cm, an optimal position of the first grating is calculated to be 48.8 cm away from the X-ray focal point by the formula (3). The optimal position of the first grating in the present exemplary embodiment indicates a position with which the width of each of X-ray beams incident on the detector becomes minimum. When the distance between the second grating and the detector is 80 cm, the width of each of the secondary X-ray beams on the detector becomes approximately 290 μm. However, when the first grating and the second grating are arranged at the above positions, the allowable error (dx) for the arrangement position of the second grating in the x-axis direction becomes zero. Therefore, such arrangement is not realistic in view of the fabrication of the system. When taking into consideration a 20 μm of allowable error of the arrangement position of the second grating in the x-axis direction, the arrangement position of the first grating in the z-axis direction is approximately 50 cm away from the X-ray focal point. Therefore, a first grating that has a focusing point located 50 cm away from the first grating is used so that the X-ray focal point lies on the focusing position of the first grating.

Secondary X-ray beams divided by the second grating are directed to a specimen which is arranged directly behind the second grating. The refraction amount of each of the secondary X-ray beams which have passed through the specimen is detected using a two-dimensional flat panel detector. The detector is arranged so that each of the secondary X-ray beams extends across a plurality of pixels of the detector. The refraction amount of each of the secondary X-ray beams can be obtained on the basis of the intensity distribution on the respective pixels of the detector. Since the secondary X-ray beams are directed to the specimen in the present exemplary embodiment, it is not possible to acquire information regarding gaps between regions through which the secondary X-ray beams pass in the entire specimen. Therefore, the secondary X-ray beams or the specimen is moved to thereby scan the specimen with the secondary X-ray beams. As a result, it is possible to increase the amount of information of the specimen to be obtained. When scanning the second grating, the detector is preferably scanned through a distance calculated by correcting an enlargement ratio $((L1+L2+L3)/(L1+L2))$ with respect to the scanned distance of the second grating.

[Second Exemplary Embodiment]

Figure 11:
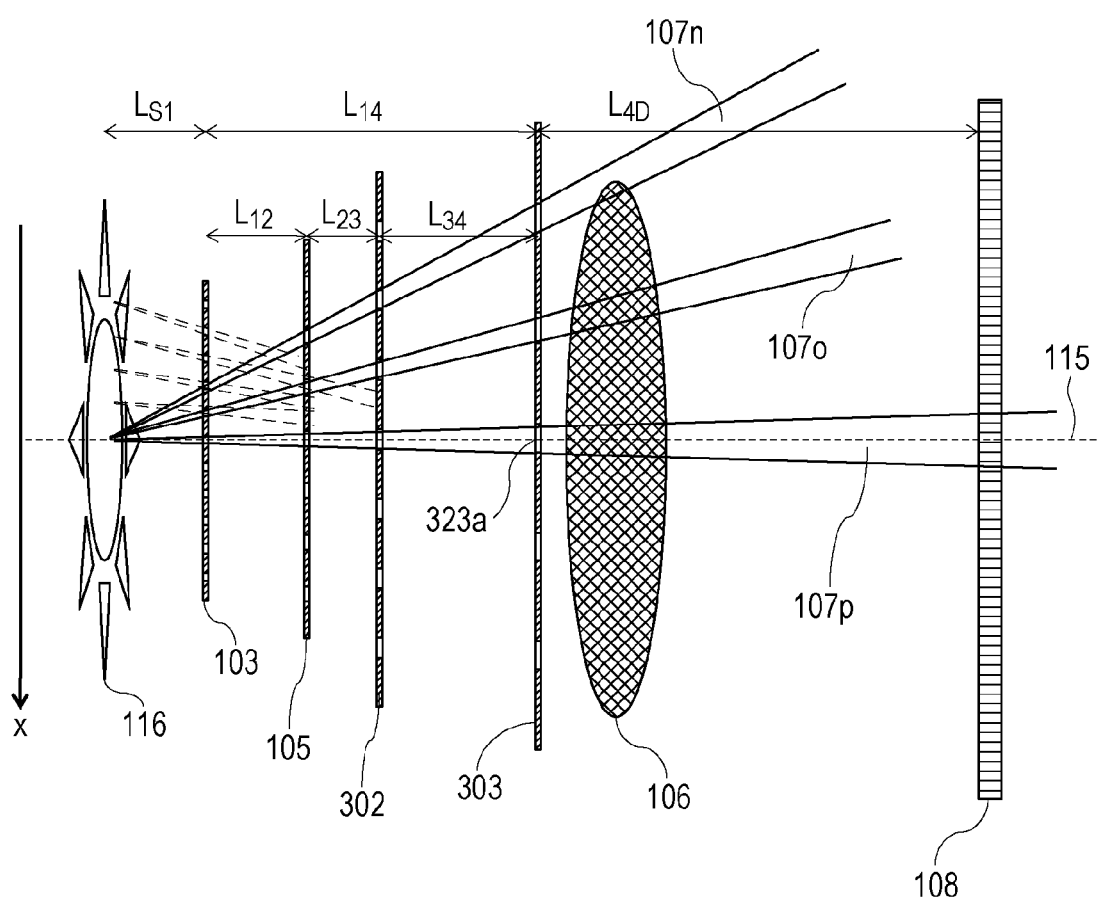
FIG. 11 is a schematic view of gratings and X-ray beams according to a second exemplary embodiment of the present invention.

In the present exemplary embodiment, a specimen information acquisition system that uses four gratings in the first embodiment will be described. The configuration of the specimen information acquisition system of the present exemplary embodiment is the same as that in the first exemplary embodiment excepting the arrangement and the number of gratings as shown in FIG. 11. However, it should be noted that since the number of gratings is larger than the first embodiment, reference numerals which denote the distances between the respective components (such as L1 and L2) are different from those in the first and second embodiments, and the first exemplary embodiment. A specimen can be placed at any positions between the X-ray focal point and the detector. However, since the number of gratings is larger than the first exemplary embodiment, and the distances between the respective gratings therefore become narrower, it is preferred to place the specimen between a fourth grating and the detector as shown in FIG. 11. With the configuration of the system of a second exemplary embodiment, the width of each of the X-ray beams incident on the detector is expressed by the following formula (18). The width depends on an opening width Ga1 of the first grating, an opening width Ga4 of the fourth grating, a distance L14 between the center of the first grating and the center of the fourth grating, and a distance L4D between the center of the fourth grating and the center of a detection surface of the detector.

[Expression 18]

$$Bs = Ga4 + \frac{L4D}{L14}(Ga1 + Ga4) \quad \text{formula (18)}$$

A second grating and a third grating in the present exemplary embodiment are provided not so much for determining the width of an X-ray beam (a quaternary beam) to be directed to the detector, but for blocking X-rays indicated by broken lines in FIG. 11. If there is no second grating and third grating in the present exemplary embodiment, the X-rays indicated by broken lines enter one transmitting portion 323a of the fourth grating, and a plurality of quaternary beams are thereby generated therethrough.

When the first grating, the second grating, the third grating and the fourth grating have the relationship expressed by the following formula (19), the system design can be made simple.

[Expression 19]

$$Ga1 + Gb1 = \frac{Ls1}{Ls1+L12}(Ga2+Gb2) = \frac{Ls1}{Ls1+L12+L23}(Ga3+Gb3) = \frac{Ls1}{Ls1+L12+L23+L34}(Ga4+Gb4) \quad \text{formula (19)}$$

The formula (19) expresses that a pitch (the sum of the width of one transmitting portion and the width of one blocking portion) of the first grating projected on the second grating is equal to a pitch of the second grating. Further, the formula (19) expresses that a pitch of the first grating projected on the third grating is equal to a pitch of the third grating, and a pitch of the first grating projected on the fourth grating is equal to a pitch of the fourth grating.

Further, it is preferred that the following formulae (20) and (21) hold.

[Expression 20]

$$Ga1 = \frac{Ls1}{Ls1+L12}(Ga2) = \frac{Ls1}{Ls1+L12+L23}(Ga3) = \frac{Ls1}{Ls1+L12+L23+L34}(Ga4)$$

formula (20)

[Expression 21]

$$Gb1 = \frac{Ls1}{Ls1+L12}(Gb2) = \frac{Ls1}{Ls1+L12+L23}(Gb3) = \frac{Ls1}{Ls1+L12+L23+L34}(Gb4)$$

formula (21)

The formula (21) is one in which the transmitting portion is replaced with the blocking portion in the formula (20). In this regard, the distance between the center of the X-ray focal point and the center of the first grating is denoted by Ls1, the distance between the center of the first grating and the center of the second grating is denoted by L12, the distance between the center of the second grating and the center of the third grating is denoted by L23, and the distance between the center of the third grating and the center of the fourth grating is denoted by L34.

In the present exemplary embodiment, since more gratings than the first exemplary embodiment are used, it is possible to arrange the first grating so as to be closer to the X-ray focal point. As a result, the width of each of the X-ray beams incident on the detector can be made smaller than that in the first exemplary embodiment. The size of the effective focal point of the X-ray source is 300 µm, the vibration amount of the X-ray focal point is 5 µm, and the width of the hem of the X-ray focal point is 150 µm. Further, in the fourth grating, the width of each of transmitting portions is 60 µm, and the distance between the focusing position and the fourth grating is 80 cm. The width of each of the transmitting portions of the first grating is 15 µm. The distance between the center of the X-ray focal point and the center of the fourth grating (LS1+L14) is 80 cm, and the distance between the center of the fourth grating and the center of the detection surface of the detector (L4D) is 80 cm. Further, the distance between the center of the X-ray focal point and the center of the first grating (Ls1) is 20 cm. Under the above condition, the width of each of the X-ray beams on the detector is calculated to be 115 µm by the formula (18). Under the same condition, the width of each of the X-ray beams on the detector in the first exemplary embodiment is 175 µm. Therefore, in the present exemplary embodiment, it is possible to obtain an X-ray beam having a width that is approximately two thirds the width of the X-ray beam in the first exemplary embodiment by using the second grating and the third grating. However, it is necessary to arrange the second grating at a position 36 to 40 cm away from the X-ray focal point and the third grating at a position 48 to 52 cm away from the X-ray focal point. It can be calculated by the formula (20) that when the second grating is arranged at a position 38 cm away from the X-ray focal point, it is preferred that the width of each of the transmitting portions of the second grating be 28.5 µm, and the width of each of the blocking portions of the second grating be 66.5 µm. Similarly, when the third grating is arranged at a position 50 cm away from the X-ray focal point, it is preferred that the width of each of the transmitting portions of the third grating be 37.5 µm and the width of each of the blocking portions of the third grating be 87.5 µm.

Since the number of gratings is four in the present exemplary embodiment, the allowable error for the arrangement position of each of the gratings in the x-axis direction tends to be smaller than that in the first exemplary embodiment. However, the increase in the number of gratings makes it possible to achieve a specimen information acquisition system that uses an X-ray source having 1 mm or larger effective focal point size which is currently used as a common medical X-ray source.

[Third Exemplary Embodiment]

In a second exemplary embodiment, a method for detecting, at the same time in two dimensions, the position change of an X-ray beam using the specimen information acquisition system of the first embodiment will be specifically described. The configuration of the specimen information acquisition system of the present exemplary embodiment is the same as that of the specimen information acquisition system of the first exemplary embodiment excepting the use of two-dimensional gratings.

Each of gratings in the present exemplary embodiment is fabricated using two one-dimensional gratings. More specifically, two one-dimensional gratings are used to construct the first grating, and two one-dimensional gratings are used to construct the second grating. Each of the two one-dimensional gratings which constitute the first grating used herein has transmitting portions each having a width of 30 µm. Further, each of the two one-dimensional gratings which constitute the second grating used herein has transmitting portions each having a width of 60 µm, blocking portions each having a width of 140 µm, and a focusing position which is located 80 cm away from the surface of the second grating. The width of each of blocking portions of the one-dimensional gratings which constitute the first grating and a focusing point thereof will be described later.

Each of the first grating and the second grating is configured in such a manner that the two one-dimensional gratings are arranged so that an alignment direction of blocking portions and transmitting portions of a first one-dimensional grating and an alignment direction of blocking portions and transmitting portions of a second one-dimensional grating are perpendicular to each other, and the two one-dimensional gratings are in contact with each other. The two one-dimensional gratings are arranged so as to be in contact with each other in order to arrange the two one-dimensional gratings so that the focusing positions of the respective two one-dimensional gratings are positioned close to each other as far as possible. In actuality, the focusing positions of the respective two one-dimensional gratings are deviated from each other by the thickness thereof. However, this level of deviation is within the fabrication error and can therefore be ignored.

X-rays which have entered each of the first grating and the second grating can pass through only a part in which the transmitting portions of the first one-dimensional grating and the transmitting portions of the second one-dimensional grating spatially overlap each other in the two one-dimensional gratings. Therefore, X-ray beams formed through the two one-dimensional gratings are in two-dimensional dot array form.

When the width of each of the transmitting portions of the first one-dimensional grating is equal to that of the second one-dimensional grating as well as the width of each of the blocking portions of the first one-dimensional grating is equal to that of the second one-dimensional grating in the two one-dimensional gratings constituting each of the two-dimensional first grating and the two-dimensional second grating, the arrangement positions of the first grating and the second grating in the z-axis direction can be determined using the formula (3). The focusing positions of the respective two one-dimensional gratings constituting the second grating are located at a position 80 cm away from the one-dimensional gratings. Therefore, the distance between the center of the X-ray focal point and the center of the second grating (L1+ L2) is determined to be 80 cm when using the formula (3). As a result, it is found that the first grating should be arranged so that the distance between the center of the X-ray focal point and the center of the first grating (L1) becomes 50 cm.

In the present exemplary embodiment, the width of each of the transmitting portions of the first one-dimensional grating is equal to that of the second one-dimensional grating as well as the width of each of the blocking portions of the first one-dimensional grating is equal to that of the second one-dimensional grating in the two one-dimensional gratings constituting each of the two-dimensional grating. However, they are not necessarily equal to each other. Important factors in the present exemplary embodiment are the following two points.

(1) One of the one-dimensional gratings of the first grating and one of the one-dimensional gratings of the second grating each of which divides X-ray beams in the x-axis direction satisfy the conditions of the formula (1) and the formula (3).

(2) The other one-dimensional grating of the first grating and the other one-dimensional grating of the second grating each of which divides X-ray beams in the y-axis direction satisfy the conditions of the formula (1) and the formula (3).

Therefore, the distance between the one-dimensional grating dividing X-ray beams in the x-axis direction and the X-ray focal point and the distance between the one-dimensional grating dividing X-ray beams in the y-axis direction and the X-ray focal point may be different from each other. On the other hand, X-rays may be two-dimensionally divided by a single two-dimensional grating having blocking portions and transmitting portions which are aligned in the two-dimensional direction. In this case, an interval between the transmitting portions in the x-axis direction is preferably equal to that in the y-axis direction, and an interval between the blocking portions in the x-axis direction is preferably equal to that in the y-axis direction.

[Fourth Exemplary Embodiment]

In a fourth exemplary embodiment, the second embodiment will be more specifically described. The configuration of a specimen information acquisition system of the present exemplary embodiment is the same as that of the specimen information acquisition system of the first exemplary embodiment excepting the configurations and the arrangement positions of the first grating and the second grating.

The size of the effective focal point of the X-ray source is 300 µm, the vibration amount of the X-ray focal point is 6 µm, and the width of the hem of the X-ray focal point is 150 µm. Further, when the width of each of the blocking portions of the second grating is 75 µm, the distance between the X-ray focal point and the first grating is 100 cm, and the distance between the first grating and the second grating is 200 cm, the width of each of the blocking portions of the first grating is calculated to be 279 µm to 329 µm by the formula (13). In this case, the formula (6) should hold in order to make the allowable error of the arrangement positions of the first grating and the second grating in the x-axis direction maximum. Therefore, the width of each of the blocking portions of the first grating is determined to be 304 µm by the formula (6). In this case, the width of each of the primary X-ray beams on the second grating becomes the integral multiple of the sum of the width of one transmitting portion and the width of one blocking portion of the second grating from the formula (6). Therefore, when the width of each of the transmitting portions of the first grating is determined to be 100 µm, the width of each of the transmitting portions of the second grating is determined to be 26 µm.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-172012, filed Aug. 2, 2012, which is hereby incorporated by reference herein in its entirety.

What is claimed is:

1. A specimen information acquisition system comprising:
a first grating having X-ray transmitting portions and X-ray blocking portions, the first grating dividing divergent X-rays from an X-ray source to form a plurality of primary X-ray beams;
a second grating having X-ray transmitting portions and X-ray blocking portions, the second grating blocking at least a part of each of the plurality of primary X-ray beams to form a plurality of secondary X-ray beams; and
an X-ray detector detecting the plurality of secondary X-ray beams,
wherein the plurality of primary X-ray beams do not overlap each other on each of the X-ray transmitting portions of the second grating, and
wherein the first grating and the second grating are arranged so that edges of the plurality of primary X-ray beams enter the X-ray blocking portions of the second grating.

2. The specimen information acquisition system according to claim 1, wherein a part of edges of adjacent ones of the plurality of primary X-ray beams enter one of the X-ray blocking portions of the second grating.

3. The specimen information acquisition system according to claim 1, wherein the following two formulae hold:

$$\frac{L2}{L1+L2}(f+df) - \frac{L1}{L1+L2}Gb2 \leq \quad \text{[Expression 1]}$$
$$Gb1 \leq \frac{L1}{L1+L2}(f+df) + \frac{L1}{L1+L2}Gb2$$

$$\frac{L1+L2}{L1}(Ga1+Gb1) < \frac{L2}{L1}(f+df) + \frac{L1+L2}{L1}Ga1 \quad \text{[Expression 2]}$$

where

Ga1 denotes the width of each of the transmitting portions of the first grating, Gb1 denotes the width of each of the blocking portions of the first grating, Ga2 denotes the width of each of the transmitting portions of the second grating, Gb2 denotes the width of each of the blocking portions of the second grating, L1 denotes the distance between the center of an X-ray focal point of the X-ray source and the center of the first grating, L2 denotes the distance between the center of the first grating and the center of the second grating, f denotes the size of an effective focal point of the X-ray focal point, and df denotes the length that is the sum of a vibration amount of the X-ray focal point and the length of hems of the X-ray focal point, and wherein one or both of the distance between an intersecting point of a straight line passing through the center of the X-ray focal point and the center of one of the transmitting portions of the first grating with the second grating and the center of one of the transmitting portions of the second grating, the one being closest to the intersecting point, and the distance between an intersecting point of a straight line passing through the center of the X-ray focal point and the center of one of the blocking portions of the first grating with the second grating and the center of one of the blocking portions of the second grating, the one being closest to the intersecting point, are smaller than dx expressed by the following formula:

$$dx = \frac{1}{2}\left(\frac{(Ga2+Gb2)\times m + Gb2 -}{\frac{L2}{L1}(f+df+Ga1) - Ga1}\right) \quad \text{[Expression 3]}$$

where m is a minimum integer satisfying the following formula $$m \geq \frac{\frac{L2}{L1}(f+df+Ga1) + Ga1 - Gb2}{Ga2 + Gb2}. \quad \text{[Expression 4]}$$

4. The specimen information acquisition system according to claim 1, wherein the following two formulae hold:

$$\frac{L2}{L1+L2}(f+df) - \frac{L2}{L1+L2}Gb2 \leq \quad \text{[Expression 5]}$$

$$Gb1 \leq \frac{L1}{L1+L2}(f+df) + \frac{L1}{L1+L2}Gb2$$

$$\frac{L1+L2}{L1}(Ga1+Gb1) \geq \frac{L2}{L1}(f+df) + \frac{L1+L2}{L1}Ga1 \quad \text{[Expression 6]}$$

where
Ga1 denotes the width of each of the transmitting portions of the first grating,
Gb1 denotes the width of each of the blocking portions of the first grating,
Ga2 denotes the width of each of the transmitting portions of the second grating,
Gb2 denotes the width of each of the blocking portions of the second grating,
L1 denotes the distance between the center of an X-ray focal point of the X-ray source and the center of the first grating,
L2 denotes the distance between the center of the first grating and the center of the second grating,
f denotes the size of an effective focal point of the X-ray focal point, and
df denotes the length that is the sum of a vibration amount of the X-ray focal point and the length of hems of the X-ray focal point, and
wherein one or both of the distance between an intersecting point of a straight line passing through the center of the X-ray focal point and the center of one of the transmitting portions of the first grating with the second grating and the center of one of the transmitting portions of the second grating, the one being closest to the intersecting point, and the distance between an intersecting point of a straight line passing through the center of the X-ray focal point and the center of one of the blocking portions of the first grating with the second grating and the center of one of the blocking portions of the second grating, the one being closest to the intersecting point, are smaller than dx expressed by the following formula:

$$dx = \quad \text{[Expression 7]}$$

$$\frac{1}{2}\left(\frac{L2}{L1}(f+df+Ga1) + Ga1 - (Ga2+Gb2)\times n - Ga2\right)$$

where n is a maximum integer satisfying the following formula $$n \leq \frac{\frac{L2}{L1}(f+df+Ga1) + Ga1 - Gb2}{Ga2 + Gb2}. \quad \text{[Expression 8]}$$

5. The specimen information acquisition system according to claim 4, wherein the following formula holds, $$\frac{L1+L2}{L1}(Ga1+Gb1) \leq \frac{L2}{L1}(f+df) + \frac{L1+L2}{L1}Ga1, \quad \text{[Expression 9]}$$

where the left side of the formula [Expression 9] is 0.95 times the right side thereof or larger.

6. The specimen information acquisition system according to claim 1, wherein the following two formulae hold:

$$Ga1 + Gb1 = \frac{L1}{L1+L2}(Ga2+Gb2) \quad \text{[Expression 10]}$$

$$\frac{f+df+Ga1}{Ga2+2Gb2-Ga1}L2 \leq L1 \quad \text{[Expression 11]}$$

where
Ga1 denotes the width of each of the transmitting portions of the first grating,
Gb1 denotes the width of each of the blocking portions of the first grating,
Ga2 denotes the width of each of the transmitting portions of the second grating,
Gb2 denotes the width of each of the blocking portions of the second grating,
L1 denotes the distance between the center of an X-ray focal point of the X-ray source and the center of the first grating,
L2 denotes the distance between the center of the first grating and the center of the second grating,
f denotes the size of an effective focal point of the X-ray focal point, and
df denotes the length that is the sum of a vibration amount of the X-ray focal point and the length of hems of the X-ray focal point, and
wherein at least one of the distance between a straight line passing through the center of the X-ray focal point and the center of one of the transmitting portions of the first grating and the center of one of the transmitting portions of the second grating and the distance between a straight line passing through the center of the X-ray focal point and the center of one of the transmitting portions of the first grating and the center of one of the blocking portions of the second grating is smaller than dx expressed by the following formula $$dx = \frac{1}{2}\left(Ga2 + 2Gb2 - \frac{L2}{L1}(f + df + Ga1) - Ga1\right).$$ [Expression 12]

7. The specimen information acquisition system according to claim 1, further comprising:
    first moving means for moving the first grating; and
    second moving means for moving the second grating,
    wherein the first moving means allows the first grating to perform at least one of parallel movement and rotational movement, and
    the second moving means allows the second grating to perform at least one of parallel movement and rotational movement.

8. The specimen information acquisition system according to claim 1, wherein the first grating is arranged at a position 5 cm or more away from the X-ray source.

9. The specimen information acquisition system according to claim 1, wherein a specimen is arranged between the X-ray source and the X-ray detector to acquire information of the specimen.

10. The specimen information acquisition system according to claim 1, further comprising a third grating, the third grating blocking at least a part of each of the plurality of secondary X-ray beams to form a plurality of tertiary X-ray beams, wherein the X-ray detector detects the plurality of tertiary X-ray beams.

11. The specimen information acquisition system according to claim 2, wherein the following two formulae hold:

$$\frac{L2}{L1+L2}(f+df) - \frac{L1}{L1+L2}Gb2 \leq$$ [Expression 13]
$$Gb1 \leq \frac{L1}{L1+L2}(f+df) + \frac{L1}{L1+L2}Gb2$$

$$\frac{L1+L2}{L1}(Ga1 + Gb1) < \frac{L2}{L1}(f+df) + \frac{L1+L2}{L1}Ga1$$ [Expression 14]

where
Ga1 denotes the width of each of the transmitting portions of the first grating,
Gb1 denotes the width of each of the blocking portions of the first grating,
Ga2 denotes the width of each of the transmitting portions of the second grating,
Gb2 denotes the width of each of the blocking portions of the second grating,
L1 denotes the distance between the center of an X-ray focal point of the X-ray source and the center of the first grating,
L2 denotes the distance between the center of the first grating and the center of the second grating,
f denotes the size of an effective focal point of the X-ray focal point, and
df denotes the length that is the sum of a vibration amount of the X-ray focal point and the length of hems of the X-ray focal point, and
wherein one or both of the distance between an intersecting point of a straight line passing through the center of the X-ray focal point and the center of one of the transmitting portions of the first grating with the second grating and the center of one of the transmitting portions of the second grating, the one being closest to the intersecting point, and the distance between an intersecting point of a straight line passing through the center of the X-ray focal point and the center of one of the blocking portions of the first grating with the second grating and the center of one of the blocking portions of the second grating, the one being closest to the intersecting point, are smaller than dx expressed by the following formula:

$$dx = \frac{1}{2}\left((Ga2 + Gb2) \times m + Gb2 - \frac{L2}{L1}(f + df + Ga1) - Ga1\right)$$ [Expression 15]

where m is a minimum integer satisfying the following formula $$m \geq \frac{\frac{L2}{L1}(f + df + Ga1) + Ga1 - Gb2}{Ga2 + Gb2}.$$ [Expression 16]

12. The specimen information acquisition system according to claim 2, wherein the following two formulae hold:

$$\frac{L2}{L1+L2}(f+df) - \frac{L2}{L1+L2}Gb2 \leq$$ [Expression 17]
$$Gb1 \leq \frac{L1}{L1+L2}(f+df) + \frac{L1}{L1+L2}Gb2$$

$$\frac{L1+L2}{L1}(Ga1 + Gb1) \geq \frac{L2}{L1}(f+df) + \frac{L1+L2}{L1}Ga1$$ [Expression 18]

where
Ga1 denotes the width of each of the transmitting portions of the first grating,
Gb1 denotes the width of each of the blocking portions of the first grating,
Ga2 denotes the width of each of the transmitting portions of the second grating,
Gb2 denotes the width of each of the blocking portions of the second grating,
L1 denotes the distance between the center of an X-ray focal point of the X-ray source and the center of the first grating,
L2 denotes the distance between the center of the first grating and the center of the second grating,
f denotes the size of an effective focal point of the X-ray focal point, and
df denotes the length that is the sum of a vibration amount of the X-ray focal point and the length of hems of the X-ray focal point, and
wherein one or both of the distance between an intersecting point of a straight line passing through the center of the X-ray focal point and the center of one of the transmitting portions of the first grating with the second grating and the center of one of the transmitting portions of the second grating, the one being closest to the intersecting point, and the distance between an intersecting point of a straight line passing through the center of the X-ray focal point and the center of one of the blocking portions of the first grating with the second grating and the center of one of the blocking portions of the second grating, the one being closest to the intersecting point, are smaller than dx expressed by the following formula:

$$dx = \frac{1}{2}\left(\frac{L2}{L1}(f+df+Ga1)+Ga1-(Ga2+Gb2)\times n - Ga2\right)$$ [Expression 19]

where n is a maximum integer satisfying the following formula $$n \leq \frac{\frac{L2}{L1}(f+df+Ga1)+Ga1-Gb2}{Ga2+Gb2}.$$ [Expression 20]

13. The specimen information acquisition system according to claim 12, wherein the following formula holds $$\frac{L1+L2}{L1}(Ga1+Gb1) \leq \frac{L2}{L1}(f+df)+\frac{L1+L2}{L1}Ga1$$ [Expression 21]

where the left side of the formula [Expression 21] is 0.95 times the right side thereof or larger.

14. The specimen information acquisition system according to claim 2, wherein the following two formulae hold:

$$Ga1+Gb1 = \frac{L1}{L1+L2}(Ga2+Gb2)$$ [Expression 22]

$$\frac{f+df+Ga1}{Ga2+2Gb2-Ga1}L2 \leq L1$$ [Expression 23]

where

Ga1 denotes the width of each of the transmitting portions of the first grating, Gb1 denotes the width of each of the blocking portions of the first grating, Ga2 denotes the width of each of the transmitting portions of the second grating, Gb2 denotes the width of each of the blocking portions of the second grating, L1 denotes the distance between the center of an X-ray focal point of the X-ray source and the center of the first grating, L2 denotes the distance between the center of the first grating and the center of the second grating, f denotes the size of an effective focal point of the X-ray focal point, and df denotes the length that is the sum of a vibration amount of the X-ray focal point and the length of hems of the X-ray focal point, and wherein at least one of the distance between a straight line passing through the center of the X-ray focal point and the center of one of the transmitting portions of the first grating and the center of one of the transmitting portions of the second grating and the distance between a straight line passing through the center of the X-ray focal point and the center of one of the blocking portions of the first grating and the center of one of the blocking portions of the second grating is smaller than dx expressed by the following formula $$dx = \frac{1}{2}\left(Ga2+2Gb2-\frac{L2}{L1}(f+df+Ga1)-Ga1\right).$$ [Expression 24]

15. The specimen information acquisition system according to claim 2, wherein the first grating is arranged at a position 5 cm or more away from the X-ray source.

16. The specimen information acquisition system according to claim 2, wherein a specimen is arranged between the X-ray source and the X-ray detector to acquire information of the specimen.

17. The specimen information acquisition system according to claim 1 further comprising:

an X-ray source for directing divergent X-rays to the first grating, and a calculator for calculating information of a specimen arranged between the X-ray source and the X-ray detector on the basis of information output from the X-ray detector.

* * * * *